United States Patent
Rhoades

(10) Patent No.: US 7,384,405 B2
(45) Date of Patent: Jun. 10, 2008

(54) OXYGENATING COSMETIC INSTRUMENT HAVING VARIOUS NUMBERS OF HEADS

(76) Inventor: Dean L. Rhoades, 2075 N. Beverly Dr., Beverly Hills, CA (US) 90210

(*) Notice: Subject to any disclaimer, the term of this patent is extended or adjusted under 35 U.S.C. 154(b) by 301 days.

(21) Appl. No.: 10/938,087

(22) Filed: Sep. 10, 2004

(65) Prior Publication Data
US 2006/0058714 A1    Mar. 16, 2006

(51) Int. Cl.
*A61H 1/00* (2006.01)
*A61H 7/00* (2006.01)
*A61H 23/02* (2006.01)

(52) U.S. Cl. ............ 601/15; 601/73; 601/137; 601/138

(58) Field of Classification Search .......... 601/46, 601/47, 72, 73, 80, 137, 138, 135, 107–111, 601/17; 15/107; 604/1
See application file for complete search history.

(56) References Cited

U.S. PATENT DOCUMENTS

| | | | |
|---|---|---|---|
| 455,567 A * | 7/1891 | Kraft | 601/138 |
| 955,339 A * | 4/1910 | Lumsden | 601/73 |
| 2,282,700 A * | 5/1942 | Bobbroff | 15/22.1 |
| 3,092,111 A | 6/1963 | Saperstein | |
| 3,769,991 A | 11/1973 | McGrath | |
| 3,823,710 A * | 7/1974 | Borden | 433/216 |
| 4,284,533 A | 8/1981 | Imamura et al. | |
| 4,608,968 A | 9/1986 | Rosofsky | |
| 4,957,747 A | 9/1990 | Stiefel | |
| 4,969,868 A | 11/1990 | Wang | |
| 4,969,881 A | 11/1990 | Viesturs | |
| 4,992,476 A | 2/1991 | Geria | |
| 5,000,941 A | 3/1991 | Chernack | |
| 5,055,043 A | 10/1991 | Weiss et al. | |

(Continued)

FOREIGN PATENT DOCUMENTS

DE    2718158 A    11/1978

(Continued)

OTHER PUBLICATIONS

PCT Internatial Search Report dated Feb. 6, 2007, International Application No. PCT/US05/30434, International Filing Date Aug. 25, 2005, 10 pages.

*Primary Examiner*—Danton DeMille
(74) *Attorney, Agent, or Firm*—Blakey, Sokoloff, Taylor & Zafman, LLP

(57) ABSTRACT

Disclosed is an apparatus including a handle capable of manipulation by a human hand, and one or more head portions to mate to various types of treatment attachments, which may be moved over an area of skin and/or body part by a motion generator moving the head portions, and/or by a user manipulating the handle. Various suitable attachments include applicator attachments having abrasive surfaces, oxygenating attachments having pores through which oxygen may travel, brush attachments for cleaning and polishing, thermal attachments for heating and cooling, and light radiating attachments. The motion generator may move the attachments by vibrating, spinning, oscillating, or propagating sonic waves through the head portions. Thus, attachments may be attached and removed from the head portions to treating skin and/or body parts by abrasion, cleaning, polishing, lighting, or oxygenation. Moreover, during treatment abrasive composition, cleaning solution, and/or polishing solution may be applied to the skin and/or body part.

27 Claims, 8 Drawing Sheets

U.S. PATENT DOCUMENTS

| | | |
|---|---|---|
| 5,360,824 A | 11/1994 | Barker |
| 5,578,022 A | 11/1996 | Scherson et al. |
| 5,658,148 A | 8/1997 | Neuberger et al. |
| 5,679,877 A | 10/1997 | Erilli et al. |
| 5,753,245 A | 5/1998 | Fowler et al. |
| 5,788,682 A | 8/1998 | Maget |
| 5,792,090 A | 8/1998 | Ladin |
| 5,800,446 A | 9/1998 | Banuchi |
| 5,891,449 A | 4/1999 | Daniel et al. |
| 5,921,251 A | 7/1999 | Joshi |
| 5,925,002 A * | 7/1999 | Wollman ............... 601/70 |
| 6,090,085 A | 7/2000 | Mehl, Sr. et al. |
| 6,135,126 A | 10/2000 | Joshi |
| 6,139,553 A | 10/2000 | Dotan |
| 6,190,307 B1 * | 2/2001 | Tsai ....................... 600/38 |
| 6,217,327 B1 | 4/2001 | Bedi |
| 6,290,976 B1 | 9/2001 | Messenger |
| 6,294,179 B1 | 9/2001 | Lee et al. |
| 6,341,400 B1 | 1/2002 | Kobayashi et al. |
| 6,663,580 B1 * | 12/2003 | Adams ................... 601/111 |
| 2002/0090385 A1 | 7/2002 | Fox et al. |
| 2002/0156402 A1 * | 10/2002 | Woog et al. ............. 601/46 |
| 2003/0165550 A1 * | 9/2003 | Rhoades ................. 601/15 |
| 2003/0167032 A1 | 9/2003 | Ignon |
| 2003/0187462 A1 | 10/2003 | Chang |
| 2003/0208159 A1 | 11/2003 | Ignon et al. |
| 2003/0212415 A1 | 11/2003 | Karasiuk |
| 2004/0193079 A1 * | 9/2004 | Siddhartha ............... 601/72 |
| 2004/0249320 A1 * | 12/2004 | Yamazaki et al. ........ 601/46 |

FOREIGN PATENT DOCUMENTS

| | | |
|---|---|---|
| EP | 0336900 A | 10/1989 |
| EP | 0571193 A | 11/1993 |
| FR | 2564318 A | 11/1985 |
| GB | 1021276 A | 3/1966 |
| WO | WO9221306 A | 12/1992 |
| WO | WO99/21532 | 6/1999 |

* cited by examiner

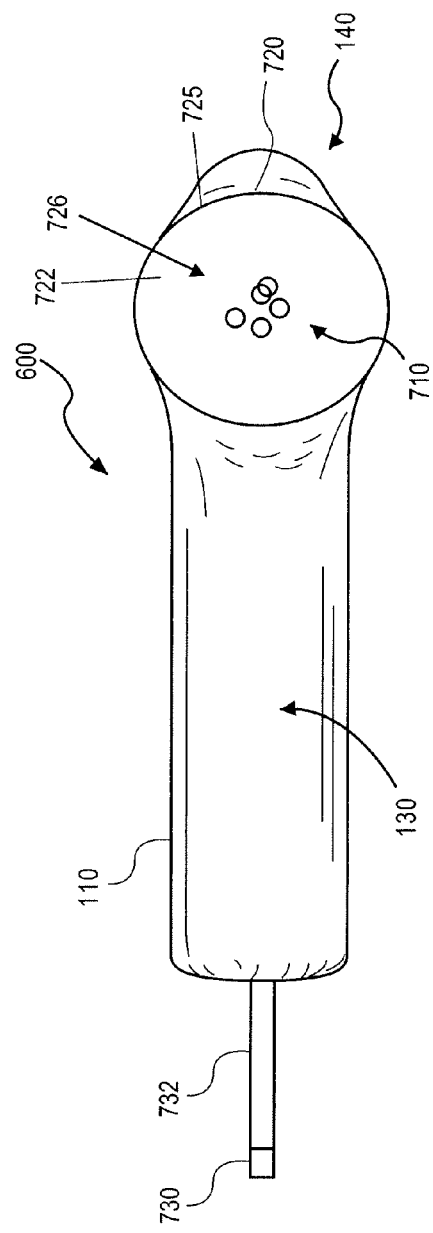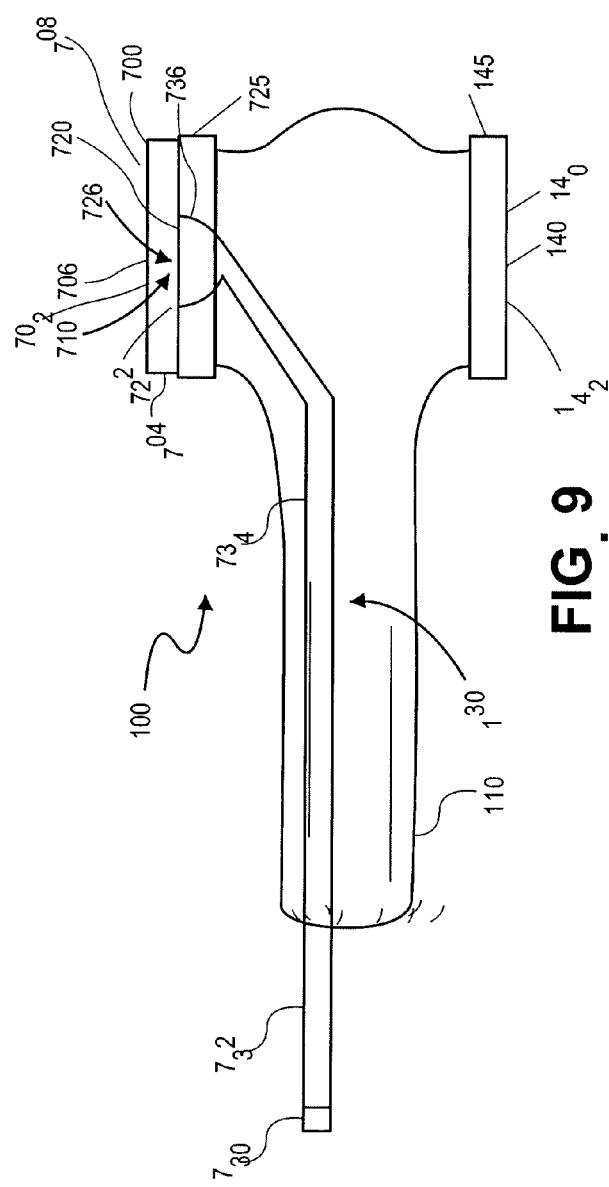

OXYGENATING COSMETIC INSTRUMENT HAVING VARIOUS NUMBERS OF HEADS

BACKGROUND

1. Field

The embodiments disclosed herein relate generally to skin and body treatment.

2. Background

Facial skin rejuvenation has been accomplished by chemical treatment referred to as "chemical peels" or laser treatment referred to as "laser surgery" and exfoliation by machine driven methods, such as with emery paper. Such methods generally require medical supervision and involve some risk of deleterious side effects as well as pain and discomfort during treatment. These methods all require long recovery time between treatments.

Microdermabrasion (e.g., microexfoliation, particle skin resurfacing) is a technique in skin care in which a controlled exfoliation of the skin is performed to improve and remove skin abnormalities. A typical spa microdermabrasion machine consists of a vacuum pump compressor that draws crystals of corundum (aluminum oxide or alumina) from a container through an output tube into a hand piece. When the hand piece is applied to skin it creates a path wherein crystals are drawn across the skin into a suction tube that leads to a disposal container for the used crystals and abraded skin (e.g., abraded skin such as to exfoliate skin). A filter in the suction tube protects moving parts of the vacuum pump. A technician manipulates the hand piece over the skin of the subject to induce exfoliation.

In addition to the noted facial skin rejuvenation, many individuals seek various treatments to rejuvenate or recondition or otherwise modify their skin and body, including their face, limbs, torso, hands, feet, scalp, hair, nails, cuticles, and other parts of the human body. Representative treatments include moisturizing treatments, hair removal and callus reduction or conditioning (e.g., softening), particularly on hands and feet.

DESCRIPTION OF THE DRAWINGS

Various embodiments are illustrated by way of example and not by way of limitation in the figures of the accompanying drawings in which like references indicate similar elements. It should be noted that references to "an," "one," "the," "other," "alternative," or "various" embodiments in this disclosure are not necessarily to the same embodiment, and such references mean at least one.

FIG. 8 is a schematic plan view of an embodiment of an apparatus having two head portions, where one head portion has openings there-through.

FIG. 9 is a schematic side cross-sectional view of the apparatus of FIG. 8.

DETAILED DESCRIPTION

Figure 1:
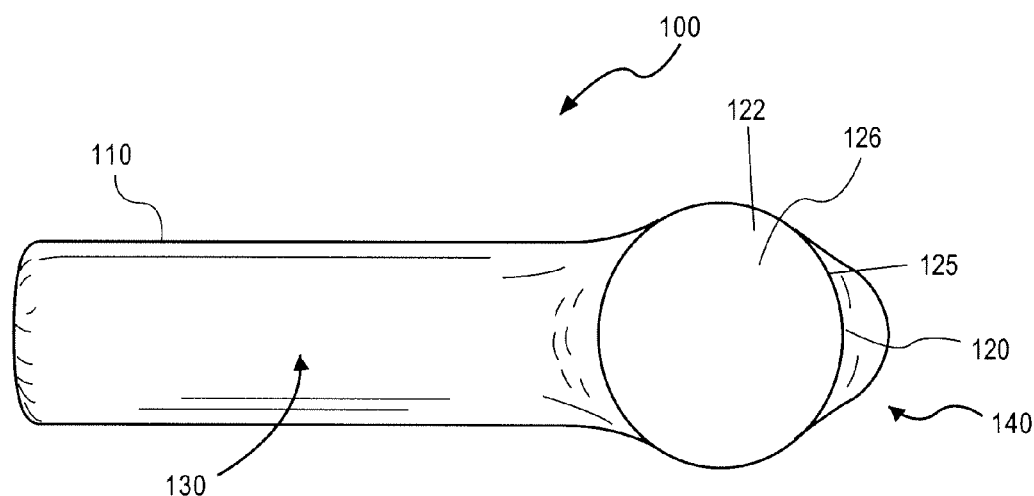
FIG. 1 is a schematic plan view of one embodiment of an apparatus having two head portions.

The following paragraphs describe embodiments of compositions, devices, and attachments that may be used, in one aspect, in treating, cosmetically treating, heat treating, cold treating, light treating, oxygen treating, rejuvenating, cleaning, and/or polishing human skin and body parts of a human body. For example, as used herein, a body part may including the face, neck, limbs, torso, hands, feet, elbows, knees, ears, scalp, hair, nails, cuticles, and other body parts of a human being.

In one embodiment, a composition is disclosed including a base and a number of abrasive particles. In one embodiment, the composition includes a base including a moisturizer suitable for application to human skin and a number of abrasive particles. Suitable abrasive particles include, but are not limited to, inorganic particles such as aluminum oxide (e.g., corundum, alumina, $Al_2O_3$), silicon carbide, silicon carbide coated particles, magnesium oxide (e.g., MgO), alumina zirconia, ceramics, plastic, and precious stones including, but not limited to, diamond, garnet, sapphire, ruby, emerald, and topaz. It is also considered that the abrasive particles may include naturally occurring particles, pumice, pumicite, perlite, reticulite, tephra, lima, zeolite, obsidian, sand, other volcanic rock, glass, metal, and particles having a hardness of greater than three on the hardness scale. Also, appropriate abrasive particles may include one or more gemstones including agate, alexandrite, amethyst, ametrine, andalusite, andradite, apatite, aquamarine, axinite, bi color tourmaline, bixbite, chalcedony, chrome tourmaline, chrysoberyl, chrysoberyl cats eye, chrysocolla quartz, chrysoprase, clinohumite, color change garnet, color change sapphire, danburite, demantoid, diamond, dinosaur bone, dioptase, emerald, enstatite, epidote, fibrolite, fire agate, fluorite, fresh water pearls, garnet, grossularite, hemimorphite, hessonite, idocrase, intarsia, iolite, kornerupine, kunzite, kyanite, lapis, malachite, malaia garnet, mali garnet, mawsitsit, moonstone, morganite, natrolite, opal, peridot, pezzottaite, phenakite, prehnite, quartz, rhodolite, rubelite, ruby, sapphire, sapphirine, scapolite, fused silica, spessartite, sphalerite, sphene, spinel, star sapphire, taaffeite, tanzanite, topaz, tourmaline, tsavorite, turquoise, and zircon. Moreover, an embodiment of the composition can have one or more type of abrasive particles.

In one embodiment, the abrasive particles are in a crystalline form. Representatively, the abrasive particles are microcrystals having an average particle size on the order of 34 microns (μm) to 556 μm (320 to 30 grit). Also, the average particle size of the microcrystals may be on the order of about 42 μm to 198 μm (280 to 60 grit). Representatively, the average particle size of the microcrystals may be on the order of about 60 grit to 80 grit for callus softening.

In one embodiment, the average particle size is less than 125 µm, such as by having an average particle size of 40 µm, 50 µm, 60 µm, 70 µm, 80 µm, 90 µm, 100 µm, 110 µm, or 120 µm. Also, the average particles size may be a grit size of between 320 and 30 grit.

When rubbed on the skin, the abrasive nature of the particles in the composition render the composition suitable as a rejuvenator (e.g., exfoliator) to improve the look and feel of an area of human skin and remove skin abnormalities. The abrasive particles dispersed in the composition tend to remove the outer layer of skin (the epidermis) to expose an underlayer of skin. In one embodiment, the particles polish the surface of the skin smooth. It is also contemplated that the particles may be used to treat a body part of a human body, as described above.

It is considered that the abrasive particles may be applied and may abrade using an applicator or brush, such as an applicator attachment, porous attachment, oxygenating attachment, or brush attachment described below. For instance, the composition may be applied to the skin and then moved across the skin using a treatment attachment or applicator, such as by rubbing into the skin, to work the composition into the skin. Alternatively, the composition may be applied to a treatment attachment or an applicator, and applied to, moved across, and rubbed into the skin using the treatment attachment or applicator. Specifically, such a treatment attachment may be attached to a treatment device or tool as described herein. For instance, a handle of the treatment device may be manipulated and the treatment attachment may be moved to cause a surface or bristles of the treatment attachment attached to the treat device to abrade an area of human skin and body parts with the abrasive particles (e.g., such as to remove, exfoliate, or abraded skin body part cells). Also, a composition containing the abrasive particles may be part of a substance such as a powder; a liquid (e.g., such as by being suspended in a base solution); a cleaning solution; a polishing solution; on a surface of an applicator, oxygenating attachment, or porous attachment (e.g., such as by being attached to that surface with an adhesive); in, on, as part of, or at the tip of bristles of a brush attachment (e.g., such as by being attached to those bristles with an adhesive). For example, a treatment attachment may be dipped into a powder, liquid, composition, or a solution having the abrasive particles.

Furthermore, according to embodiments, a cleaning composition or solution is disclosed including a cleaning agent for cleaning human skin. Suitable cleaning agents include, but are not limited to astringent, alcohol, witch-hazel, soap, grease or oil cutting solution, shampoo, dishwashing liquid, liquid soap, makeup remover, and/or other skin cleaning agents, such as for the face and neck of a person. For example, cleaning agents in a cleaning solution may or may not be dissolved in the cleaning solution. Similarly, it can be appreciated that abrasive particles in a cleaning solution may not be dissolved there-in. Moreover, an embodiment of the cleaning solution can have one or more types of cleaning agents. In some embodiments, in addition to a cleaning agent, the cleaning solution may have abrasive particles suspended therein. Suitable particles size may be driven in part by the viscosity of the cleaning composition. It is also contemplated that the cleaning composition or solution may be used to treat body parts of a human body.

The cleansing nature of the cleaning agent(s) in the cleaning composition renders the composition suitable to clean an area or layer of skin or a body part. The cleaning composition may be used to improve the look and feel of an area of human skin and remove dirt, loose cells, and exfoliated cells, from a layer or area of skin. Thus, the cleaning solution tends to clean the outer layer of skin (the epidermis) to expose a dirt free underlayer of skin. In cases where the skin has been exfoliated prior to applying the cleaning solution, use of the cleaning solution may clean the outer layer of exfoliated skin cells, abrasive particles, dirt, and other substances to expose an underlayer of skin having reduced amounts of those substances.

It is considered that the cleaning solution may be applied and may clean using a brush, such as a brush having abrasive or soft bristles. Specifically, a brush to apply and clean using the cleaning solution may be a brush attachment, oxygenating attachment, or porous attachment attached to a treatment device or tool as described herein. For instance, a handle of the treatment device may be manipulated and the brush attachment, oxygenating attachment, or porous attachment may be moved to cause the brush or other attachment surface to abrade, clean, or polish an area of human skin with the cleaning solution (e.g., such as to remove exfoliated or abraded skin particles after exfoliation, to cleans and/or polish the area of the skin). Specifically, the cleaning agent may be part of various substances and be applied to the skin and body part, directly or via the treatment attachment, such as described above for the abrasive particles.

Similarly, according to embodiments, a polishing solution or compound is disclosed including a polishing agent for polishing human skin. Suitable polishing agents include, but are not limited to lotions, astringent, alcohol, witch-hazel, the abrasive particles mentioned above, and/or other skin polishing agents, such as for the face and neck of a person. Suitable polishing agents may or may not include abrasive particles. Moreover, an embodiment of the polishing solution can have one or more types of polishing agents. It is also contemplated that the polishing solution may be used to treat body parts of a human body.

The polishing nature of the polishing agent(s) in the polishing solution render the composition suitable to polish an area or layer of skin or other body part. The polishing solution may be used to improve the look and feel of an area of human skin and polish abraded or other skin cells of a layer or area of skin. Thus, the polishing solution tends to polish the outer layer of skin (the epidermis) to make the layer smooth and shiny.

It is considered that the polishing solution may be applied and may polish using a brush, such as a brush having soft bristles. Specifically, a brush to apply and polish using the polishing solution may be a brush attachment, oxygenating attachment, or porous attachment attached to a treatment device or tool as described herein. For instance, a handle of the treatment device may be manipulated and the brush attachment, oxygenating attachment, or porous attachment may be moved to cause the brush or attachment surface to polish an area of human skin with the polishing solution (e.g., such as to smooth a cleaned area of skin after cleaning as described above). Specifically, the cleaning agent may be part of various substances and be applied to the skin or a body part directly or via the treatment attachment, such as described above for the abrasive particles.

In addition to the treatment specified above, according to embodiments, skin and body parts, as described above, may be treated by applying oxygen, illuminating with light, radiating cold into, or radiating heat onto the skin and body part. Thus, one or more (e.g., a series) of these rejuvenation, oxygenating, lighting, cooling, heating, cleansing, and/or polishing treatments may be used to improve the skin and body parts subject to the treatment. Such improvements include improvement in the appearance of fine lines, wrinkles, stretch marks, acne, large pores, sluggish skin, non-inflammatory acne, acne scars, surgical scars, rough or coarse textured skin, age spots, blotchy skin conditions, burns, wounds, abrades, and sun damaged skin. In addition, such treatments include rejuvenation, cleansing, and/or polishing of the skin to soften the skin, smooth the skin, sooth the skin. For example, one or more treatments may be used to treat the skin and body parts, such as to improve the appearance and texture of the skin and reducing roughness, rough patches, and callused skin.

In one embodiment, the tool or device may be a portable apparatus suitable for contacting the skin and/or body parts, where the apparatus has an applicator attachment removably attached to one moveable head portion and a brush attachment removably attached to another moveable head portion. The applicator attachment and brush attachment have dimensions suitable for contacting body parts and/or localized areas of human skin, such as areas of the face, neck, hair, cuticles, nails, scalp, limbs, torso, hands and feet. For example, the applicator attachment and brush attachment may be used to treat acne, and/or acne scars, such as on the face, neck, back, and chest of a person.

Figure 2:
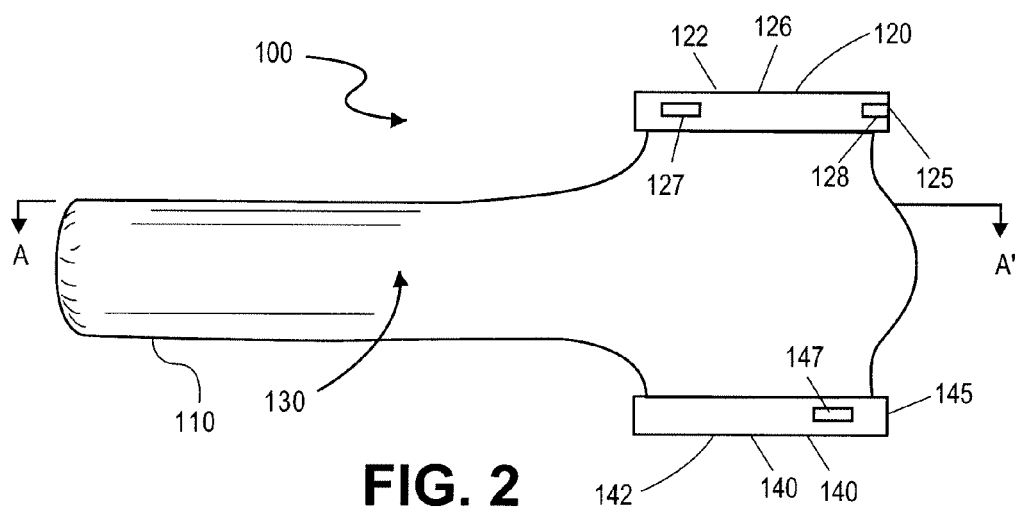
FIG. 2 is a schematic side view of the apparatus of FIG. 1.

FIG. 1 is a schematic plan view of one embodiment of an apparatus having two head portions. FIG. 2 is a schematic side view of the apparatus of FIG. 1. Referring to the example shown in FIG. 1 and FIG. 2, apparatus 100 includes device or tool 110 having handle portion 130, head portion 120 and head portion 140. Head portions 120 and 140 are opposite each other in embodiments. Treatment attachments may be removably attached to head portion 120 and head portion 140, as will be described further below with respect to FIGS. 4-12.

According to embodiments, there may be between one and four head portions, such as for a device or tool having three or four head portions similar to head portions 120 and 140. Thus, in a device having three head portions, a view from above the device looking down along a longitudinal axis of the handle would show a triangular arrangement or orientation of the head portions. Similarly, in a device having four head portions, a view from above the device looking down along a longitudinal axis of the handle would show a square arrangement or orientation of the head portions. Moreover, each head portion of a device having between one and four head portions may be a head portion and may have a treatment attachment attached thereto, as described herein for head portion 120 and treatment attachments to attach thereto.

For example, as shown in FIG. 1 and FIG. 2, head portion 120 has exterior sidewall 125, exterior surface 126, and first end 122 onto which may be mounted a treatment attachment to treat an area of human skin or a body part. In addition, exterior sidewall 125 is shown with recesses 127 and 128, such as recesses to be engaged by protuberances of a treatment attachment to be mounted on head portion 120 (e.g., also described below or FIGS. 6-7).

Similarly, as shown in FIG. 1 and FIG. 2, head portion 140 has exterior sidewall 145, exterior surface 146, and first end 142 onto which may be mounted a treatment attachment to treat an area of human skin or a body part. In addition, exterior sidewall 145 is shown with recess 147, such as recesses to be engaged by protuberances of a treatment attachment to be mounted on head portion 140 (e.g., also described below or FIGS. 6-7). Thus, device or tool 110 may then be positioned, oriented or reoriented to use a treatment device attached to head portion 120, and then positioned, oriented or reoriented to use a treatment device attached to head portion 140, or vice versa.

Additionally, according to embodiments, head portion 140, exterior sidewall 125, exterior surface 146, first end 142, recess 147, and features and functions thereof may correspond to similar structures head portion 120, exterior sidewall 125, exterior surface 126, first end 122, recess 127, and features and functions thereof as described herein. Specifically, those features may be the same size as their corresponding feature on the other head. Thus, treatment devices may be attached to, removed from, and switch between (e.g., such as by being interchangeably mountable on head portion 120 as well as head portion 140) head portion 120 and head portion 140.

In another embodiment, head portion 120 has a different attachment mechanism than head portion 140 so that only a subset of treatment attachments will attach thereto. For example, a brush attachment or abrasive applicator pad attachment may mate properly with head portion 120, but not head portion 140; while a sponge applicator attachment may mate properly with head portion 140, but not head portion 120.

Device or tool 110 may be a dynamic device or tool in the sense that it includes moveable parts such as a device that vibrates or otherwise moves a portion of device or tool 110, such as head portion 120 and/or head portion 140. The dynamic device or tool may be powered by fixed or moveable internal power supply such as battery power, or an external source such as a cord connected to a wall outlet. Moreover, device or tool 110 may be powered by a direct current ("DC") battery or by an alternating current ("AC") power source. In addition, the power source or batteries of device or tool 110 may be charged by a charger as explained further below with respect to FIGS. 4A and 4B. Also, the dynamic device or tool may be powered by an internal power supply such as mechanical power involving a spring and a pull cord, rubber band, or winder to wind the spring.

Handle portion 130 is capable of manipulation by a human hand and is suitable for gripping by a human hand, for example, with at least one finger of an adult human hand capable of extending around handle portion 130 to contact a thumb of the same hand. In this manner, device or tool 110 is of a size such that it may be maneuvered within a human hand. In one embodiment, handle portion 130 is adapted, at least for a dynamic device, to house in an interior volume, a removable/replaceable power source, such as batteries (e.g., one or more AA batteries, or nickel metal hydride batteries), optional circuitry for coupling to an AC power source, and circuitry to operate a motor (e.g., DC) driven apparatus. Device or tool 110, including handle portion 130 and head portion 140, in one embodiment, is formed of a plastic casing. In another embodiment, the casing may be metallic, wood, composite, plastic, or rubber.

Figure 3:
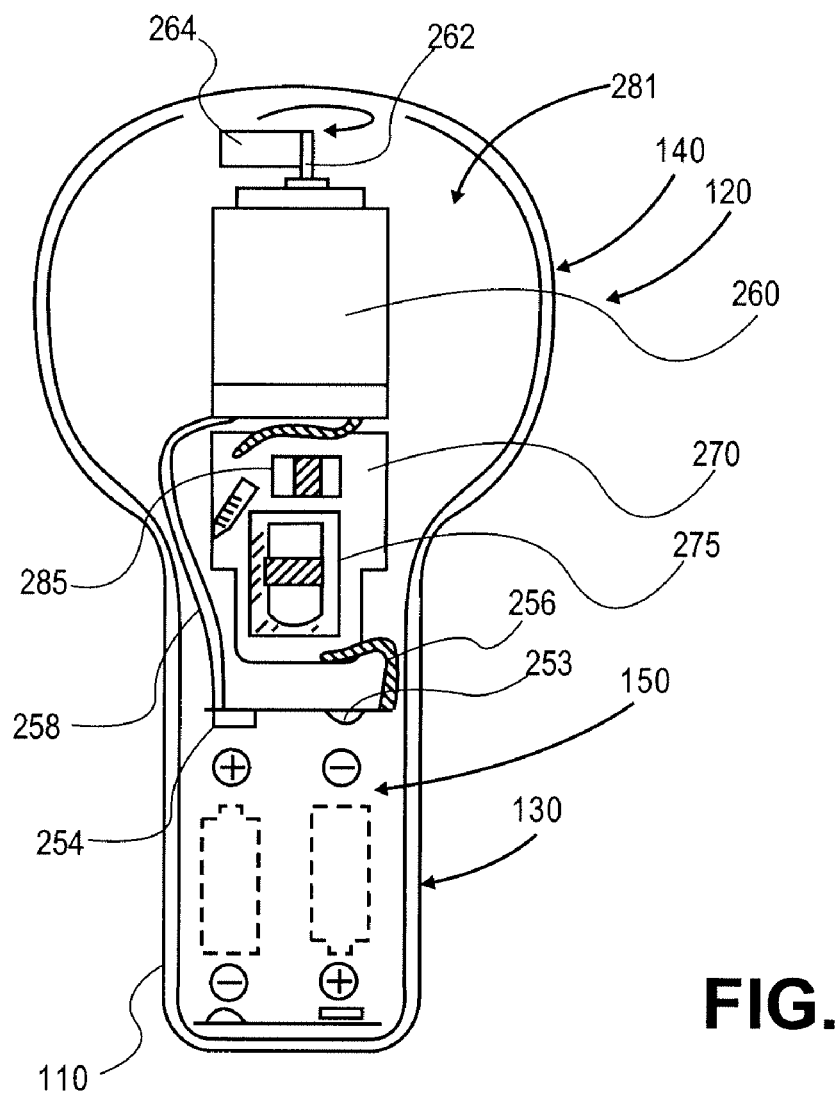
FIG. 3 shows a schematic cross-sectional view of an embodiment of the apparatus through line A-A of FIG. 2.

FIG. 3 shows a schematic cross-sectional view of an embodiment of device or tool 110 through line A-A of FIG. 2, specifically illustrating a dynamic device including, in this embodiment, a mechanism to vibrate head portions 120 and 140 of device or tool 110. In this embodiment, device or tool 110 includes handle portion 130 having interior chamber 251 to accommodate a removable power source. In one example, the power source is two AA batteries that fit within interior chamber 251 of handle portion 130. A location of conductors 253 and 254 define an end of the interior chamber 251. Leads 256 and 258 are connected to conductors 253 and 254, respectively, and bring current to/from motor 260. Lead 256 is coupled to circuit board 270 that includes switch 275 to control the operation of motor 260.

Switch 275 may be a two-position switch (ON/OFF) or a multiple position switch for operating motor 260 at multiple or veritable speeds.

Motor 260 is positioned, in this example, in interior portion 281 of head portions 120 and 140 of device or tool 110 and includes shaft 262 extending from one end of motor 260. Shaft 262 is rotated (as illustrated) with the operation of motor 260. It is contemplated that motor 260 and/or a motion generator may be located within device or tool 110 at various orientations, such as sideways, lengthwise, upwards pointing, or downwards pointing with respect to an arrow drawn along the longitudinal axis from handle 130 towards a median point between head portion 120 and 140.

Connected to an end of shaft 262 of motor 260 is eccentric mass 264. In this embodiment, eccentric mass 264 is a semi-cylindrical body coupled at its axis to shaft 262. In this manner, as eccentric mass 264 rotates, its shape generates a rhythmic motion in head portions 120 and 140 of device or tool 110 producing a vibration.

Motor 260 and eccentric mass 264 may be designed to move at the first head portion or the second head portion. For example, device or tool 110 may include motion selection switch 285 to select movement of either head portion 120 or head portion 140 at one time. It is also contemplated that switch 285 may include a selection to move both head portion 120 and head portion 140 at one time. Alternatively, device or tool 110 may not include a motion selection switch 285, but may have both head portion 120 and head portion 140 moving at the same time.

Moreover, it is contemplated that instead of motor 260 and eccentric mass 264, device or tool 110 may include a motion generator without a motor, such as a sonic wave generator to propagate sonic and/or ultrasonic waves through head portion 120 and/or head portion 140. Such a sonic generator may be powered by an internal, external, rechargeable, mechanical and/or electrical power source as noted above.

It is also contemplated that device or tool 110 may include a motion generator to spin head portion 120 and/or head portion 140. Similarly, the motion generator may spin one or both of the head portions back and forth, such as by spinning the head portion a partial, full, or multiple rotations in one direction, and then by spinning the head portion back by a partial, full, or multiple rotations in the opposite direction. The rotation in the first direction can be more, less or equal to the amount of rotation back in the opposite direction. Such a spinning motion generator may include motor 260 and may include switch 285 to select movement of head portion 120, head portion 140, or both. It is also contemplated that the motor may generate oscillating motion such as when the poling of the alternating current applied to the motor change rapidly. Such motion is generally deemed to fall within the broad category of vibratory motion. As described herein, moving of head portions and/or treatment attachments may include spinning in one direction, spinning back and forth. Furthermore, head portion and/or treatment attachments may be moved by sonic wave, ultrasonic wave, oscillating, or vibrating motion generators of device or tool 110 or may be moved by manipulating handle portion 130, oscillating, vibrating, or manually causing motion of the head portion or treatment attachment with respect to a point on skin or a body part.

Figures 4A, 4B:
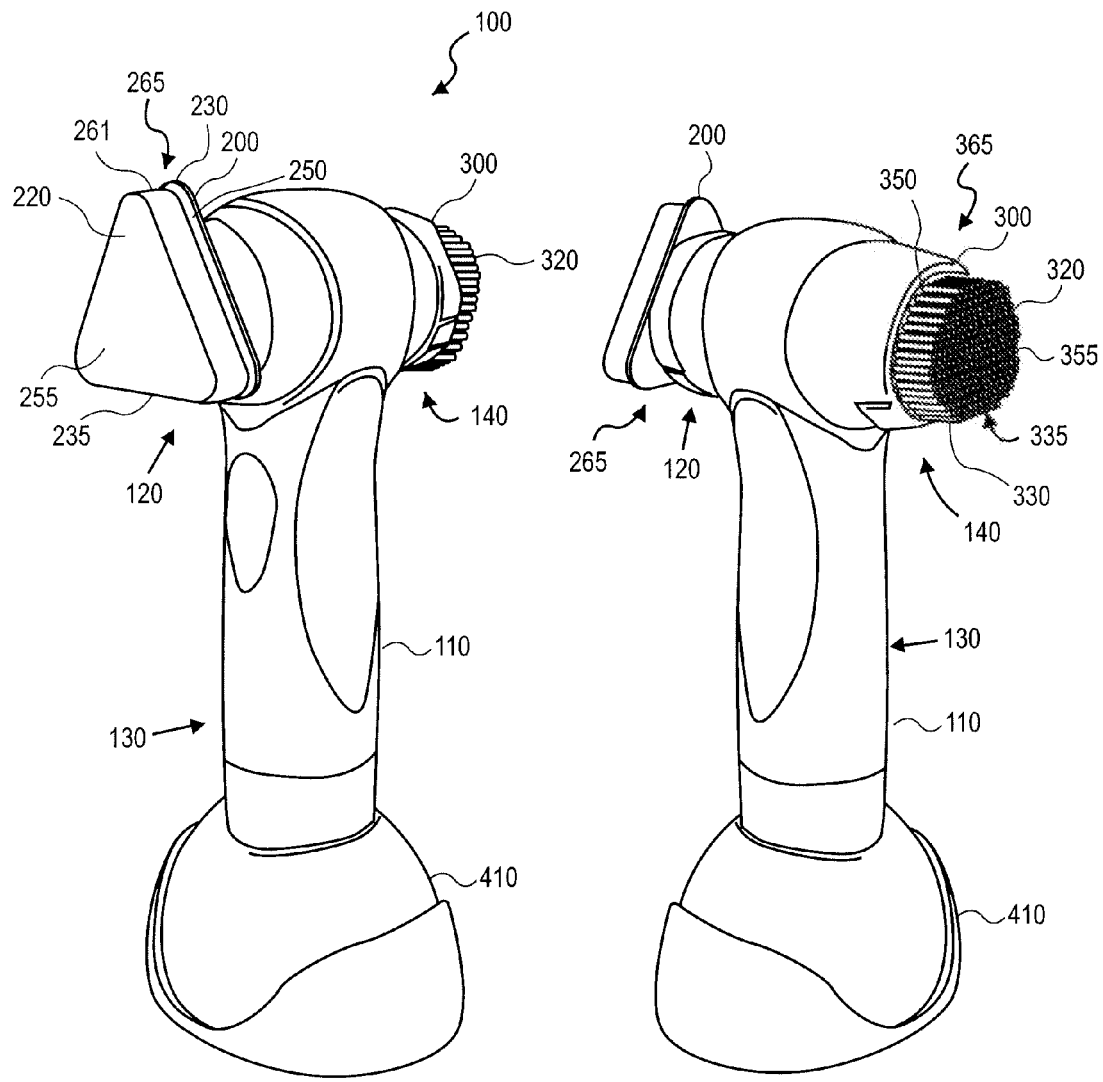
FIGS. 4A and 4B are schematic side perspective views of the apparatus of FIG. 2 having an applicator attachment coupled to one head portion and a brush attachment coupled to the other head portion.

In addition to device or tool 110, the embodiment of apparatus 100, illustrated in FIGS. 1-3, may include treatment attachments attached to head portion 120 and/or head portion 140. For instance, FIGS. 4A and 4B are schematic side perspective views of the apparatus of FIGS. 1 and 2 having an applicator attachment coupled to one head portion and a brush attachment coupled to the other head portion. FIGS. 4A and 4B show applicator attachment 200 attached to head portion 120. Applicator attachment 200 includes pad 220. Pad 220 has dimensions suitable for contacting localized areas of human skin or a body part. In one embodiment, pad 220 includes an abrasive surface, such as a surface of metal, plastic, rubber, or adhesive, having abrasive particles as described above attached thereto by adhesive, where the particles of a grit size of between 320 and 30 grit. For instance, pad 220 may have an abrasive surface including inorganic particles such as aluminum oxide (e.g., corundum, alumina, $Al_2O_3$), silicon carbide, silicon carbide coated particles, magnesium oxide (e.g., MgO), alumina zirconia, ceramics, plastic, and precious stones including, but not limited to, diamond, garnet, sapphire, ruby, emerald, and topaz. In addition, the abrasive surface may include naturally occurring particles, pumice, pumicite, perlite, reticulite, tephra, lima, zeolite, obsidian, sand, other volcanic rock, glass, metal, and particles having a hardness of greater than three on the hardness scale. Such an abrasive surface may include a plurality of abrasive particles attached to a generally planar surface. For example, appropriate abrasive particles may include one or more gemstones including agate, alexandrite, amethyst, ametrine, andalusite, andradite, apatite, aquamarine, axinite, bi color tourmaline, bixbite, chalcedony, chrome tourmaline, chrysoberyl, chrysoberyl cats eye, chrysocolla quartz, chrysoprase, clinohumite, color change garnet, color change sapphire, danburite, demantoid, diamond, dinosaur bone, dioptase, emerald, enstatite, epidote, fibrolite, fire agate, fluorite, fresh water pearls, garnet, grossularite, hemimorphite, hessonite, idocrase, intarsia, iolite, kornerupine, kunzite, kyanite, lapis, malachite, malaia garnet, mali garnet, mawsitsit, moonstone, morganite, natrolite, opal, peridot, pezzottaite, phenakite, prehnite, quartz, rhodolite, rubelite, ruby, sapphire, sapphirine, scapolite, fused silica, spessartite, sphalerite, sphene, spinel, star sapphire, taaffeite, tanzanite, topaz, tourmaline, tsavorite, turquoise, and zircon.

Pad 220 may be formed to have a desired geometry. For example, in the embodiment illustrated in FIGS. 4A and 4B, pad 220 is suitable for cosmetic and rejuvenation treatments to the face and neck of a human, such as to treat acne, large pores, sluggish skin, and/or acne scars thereon. It is appreciated that pad 220 and applicator attachment 200 are also suitable for use on areas of skin or a body part besides the face and neck (e.g., such as for use on hair, nails, cuticles, scalp, hands, feet, limbs, and torso of a person). Accordingly, pad 220 has, in this embodiment, geometry of a polygon shape such as the generally triangular shape shown in FIGS. 4A and 4B. The triangular shape allows pad 220 to be maneuvered between surfaces or in recessed areas (e.g., such as between the nose and cheeks) with a portion of the surface (e.g., an abrasive exterior surface) remaining in contact with the skin (e.g., at the base of the nose). In one embodiment, each side 235 of triangular pad 220 has a length on the order of about 1.5 to four inches (3.5 to 10 cm). In one embodiment, each corner 230 of pad 220 is blunted reducing the distance to the corner by on the order of, for example, 0.01 to 0.67 inches (0.025 to 17 mm).

In the embodiment illustrated in FIGS. 4A and 4B, pad 220 includes exterior surface portion 255 (superior surface as viewed) that includes an abrasive surface. Pad 220 also includes body 265 a portion of which includes border 250 surrounding the abrasive surface. Border 250 may include a smooth, possibly deformable surface having a rounded edge.

According to embodiments, pad 220 may have a plurality of sides, such as side 235; a plurality of corners, such as corner 230; and a border, such as border 250. Also, pad 220 may have various shapes, including a teardrop shape, or a polygon shape having a plurality of elliptically shaped corners, each corner having two points where the elliptically shaped corner deviates from two sides of the polygon, and an apex. Moreover, each of those points may be located in a range of between 0.062 inches (1.5 mm) and 0.67 inches (17 mm) from where two sides of the polygon would meet to from an apex. Also considered, are abrasive surface geometries where a width of a rounded corner where the rounding of a polygon corner begins is in a range between 0.062 inches (1.5 mm) and 0.67 inches (17 mm) in width.

For instance, in the example shown in FIGS. 4A and 4B, generally triangular shaped pad 220 has three side lengths and three rounded corners, each corner comprising an elliptical shape having a curvature initiated along two side lengths of the triangle, where the curvature is initiated in the range between 0.1 inches (2.5 mm) and 0.67 (17 mm) inches from where the two side lengths, if continued, would form an apex.

Applicator attachment 200 may also include pad 220 having cushioning layer 261 between, for example, an exterior surface and a cap component of applicator attachment 200 (described below). In the embodiment shown in FIG. 2, pad 220 includes exterior surface portion 255 (such as an abrasive surface and backing), cushioning layer 261, and body 265 that acts as a frame and/or support for exterior surface portion 255 and cushioning layer 261. As illustrated, body 265 includes border 250 (described above).

FIGS. 4A and 4B also show brush attachment 300 attached to head portion 140. Brush attachment 300 includes bristles 320 including, such as abrasive bristles made of or including one or more natural and/or synthetic-material, such as hair, plastic, nylon, polymer, metal, composite, polyurethane, latex, rubber and resin. Bristles 320 have dimensions suitable for contacting or being applied to localized areas of human skin (e.g., such as to treat acne, large pores, sluggish skin, and/or acne scars) or a body part. In one embodiment, bristles 320 form a brush for brushing an abraded area of human skin with abrasive bristles to remove exfoliated or partially abraded skin particles. In another embodiment, bristles 320 form a brush for brushing an abraded area of human skin with soft bristles to polish or cleanse areas of human skin. It is also contemplated that bristles 320 may include a combination of abrasive, non-abrasive, soft, polishing, cleansing, and/or other appropriate bristles for treating an area of human skin. Specifically, bristles 320 can have abrasive particles in, on, as part of, and/or at the tip of the bristles suitable to treat skin and body parts. Also, bristles 320 may have abrasive particles, such as aluminum oxide, imbedded in the fiber or material of the bristles, or adhered to the outer shaft of the bristles. Suitable abrasive particles include inorganic particles such as aluminum oxide (e.g., corundum, alumina, $Al_2O_3$), silicon carbide, silicon carbide coated particles, magnesium oxide (e.g., MgO), alumina zirconia, ceramics, plastic, and precious stones including, but not limited to, diamond, garnet, sapphire, ruby, emerald, and topaz. In addition, the abrasive particles may include naturally occurring particles, pumice, pumicite, perlite, reticulite, tephra, lima, zeolite, obsidian, sand, other volcanic rock, glass, metal, and particles having a hardness of greater than three on the hardness scale. Moreover, appropriate abrasive particles may include one or more gemstones including agate, alexandrite, amethyst, ametrine, andalusite, andradite, apatite, aquamarine, axinite, bi color tourmaline, bixbite, chalcedony, chrome tourmaline, chrysoberyl, chrysoberyl cats eye, chrysocolla quartz, chrysoprase, clinohumite, color change garnet, color change sapphire, danburite, demantoid, diamond, dinosaur bone, dioptase, emerald, enstatite, epidote, fibrolite, fire agate, fluorite, fresh water pearls, garnet, grossularite, hemimorphite, hessonite, idocrase, intarsia, iolite, kornerupine, kunzite, kyanite, lapis, malachite, malaia garnet, mali garnet, mawsitsit, moonstone, morganite, natrolite, opal, peridot, pezzottaite, phenakite, prehnite, quartz, rhodolite, rubelite, ruby, sapphire, sapphirine, scapolite, fused silica, spessartite, sphalerite, sphene, spinel, star sapphire, taaffeite, tanzanite, topaz, tourmaline, tsavorite, turquoise, and zircon. Bristles 320 can be a number of bristles each having a bristle thickness between 0.0001 to 0.0150 inch.

According to embodiments, bristles 320 may be used to apply a cleaning solution or a polishing solution as described above. Specifically, bristles 320 may apply a cleaning solution to and/or clean a body part, an area of skin, or a layer of skin with a cleaning solution. Moreover, bristles 320 may apply a polishing solution to and/ or polish a body part, an area of skin, or a layer of skin with a cleaning solution. It can be appreciated that bristles 320 may be used to apply both a cleaning solution and a polishing solution at the same time, or during separate times (e.g., such as to the same or different body parts, areas or layers of skin).

Bristles 320 (e.g., as either a collection of different types of bristles as described above, or as a group of an individual type of bristle as described above) may be formed to have a desired geometry, such as by having various shapes, including a polygon shaped, curved shaped, or circular shaped cross section with respect to an axis extending through the center of the head portion brush attachment 300 is mounted on and brush attachment 300. For example, in the embodiment illustrated in FIGS. 4A and 4B, bristles 320 are suitable for cosmetically treating, rejuvenation, cleansing, and/or polishing treatments (e.g., such as treatment including removing or cleaning exfoliated or abraded skin, and or treating acne, large pores, sluggish skin, and acne scars of the face and neck of a human). Moreover, bristles 320 may be used to polish cleaned or abraded skin or a body part. It is appreciated that bristles 320 and brush attachment 300 are also suitable for use on areas of skin or a body part besides face and neck (e.g., such as for use on hair, nails, cuticles, scalp, hands, feet, limbs, and torso of a person). Accordingly, bristles 320, as a group of all the bristles of brush attachment 300, have, in this embodiment, geometry of a polygon shape such as the generally hexagonal or triangular shape shown in FIGS. 4A and 4B. The hexagonal shape allows bristles 320 to be maneuvered between fingers and/or toes with a portion of brushing ends of the bristles (e.g., abrasive bristle ends of multiple bristles) remaining in contact with the skin (e.g., at the base of the nose and cheeks). In one embodiment, each side 335 of hexagonal bristles 320 has a length on the order of about 0.25 to three inches. In one embodiment, each corner 330 of bristles 320 is blunted reducing the distance to the corner by on the order of, for example, 0.01 to 0.67 inches.

In the embodiment illustrated in FIGS. 4A and 4B, bristles 320 includes brushing ends 355 (superior surface as viewed) that includes a number of abrasive bristle ends of multiple bristles. Bristles 320 also include body 365 a portion of which includes border 350 surrounding bristles 320. Border 350 may include a smooth, possibly deformable surface having a rounded edge.

Similar to the applicator attachment, bristles 320 may have a plurality of sides, such as side 335; a plurality of corners, such as corner 330; and a border, such as border 350. Bristles 320 may have a polygon shape including a plurality of elliptically shaped corners, each corner having two points where the elliptically shaped corner deviates from two sides of the polygon, and an apex.

It is contemplated that treatment attachments in addition to applicator attachment 200 and brush attachment 300 may be removably or permanently attached to head portion 120 and head portion 140. For example, such other treatment attachments include an applicator for applying cream, liquid, and/or abrasive particles; a sponge applicator; a porous mass attachment; a brush attachment without abrasive bristles; a brush attachment with abrasive bristles imbedded in the fiber of the bristles, in the tip of the bristles, or adhered to the outer shaft of the bristles; a soft pad buffer; porous attachment, oxygenating attachment 700 and porous attachment 1000 (e.g., such as an attachment to receive gas from a source of oxygen that can be an oxygen cylinder, oxygen canister, oxygen tank including oxygen gas of up to 4,000 pounds per square inch (PSI) pressure, oxygen generator, oxygen manufacturing unit, or cartridge such as a source of oxygen external or internal and within the device or tool to which the oxygenating attachment is attached, also see FIGS. 8-11); a heating unit attachment; a cooling unit attachment; a light source attachment; and a sponge pad attachment as described below. In accordance with an embodiment, either or both of the head portions may include openings to allowing oxygen and/or other gas or liquid to travel from below the head portion to a treatment attachment attached to the head portion, such as during treatment of skin and body parts with the treatment attachment (e.g., such as oxygenating attachment 700 and porous attachment 1000), as will be described further below with respect to FIGS. 8-11.

Also, according to embodiments, handle portion 130 may be designed or adapted, to be received by and stand upright in charger 410. For example charger 410 and handle portion 130 may have contacts sufficient to form an electrical connection so that a power source within handle portion 130, such as batteries, may be charged or recharged. Thus, charger 410 may include circuitry for connecting to an AC power source, and converting the AC power to appropriate power (e.g., such as DC power of a lesser voltage) to charge the power source within handle portion 130. For instance, charger 410 may be adaptable to connect to a 110 or 220 volt source of AC, such as from a wall socket. Charger 410 may be formed of a plastic casing, metal, or other material mentioned herein for forming device or tool 110, or portions thereof.

Figure 5:
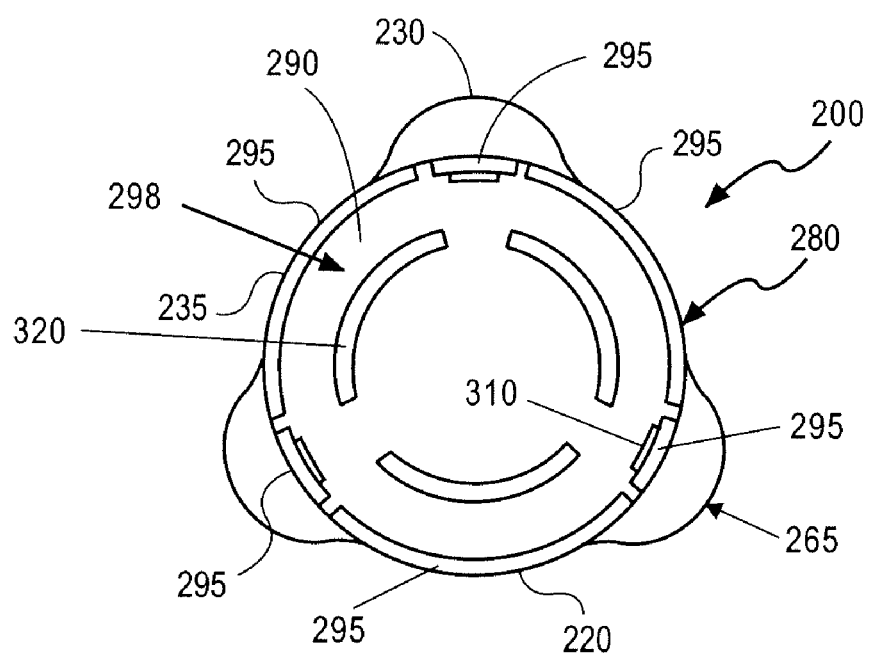
FIG. 5 is a schematic back view of the applicator attachment of FIGS. 4A and 4B prior to attachment to the head portion.

In addition, applicator attachment 200, brush attachment 300, or another treatment attachment may include a cap for removably attaching to head portion 120 or 140. According to embodiments, treatment attachments may also attach to head portions via threaded mating, magnetic attractive force, adhesive, heat bonding, tape, glue, or other sufficient attachment systems. In some cases, an oxygenating treatment attachment, porous mass attachment, or a brush attachment having openings or pores in its base, can be attached to head portions via adhesive or magnetic forces and to allow oxygen gas to flow through the attachment to treat skin or body parts with the attachment. For example, FIG. 5 is a schematic back view of the applicator attachment of FIGS. 4A and 4B prior to attachment to the head portion. FIG. 5 shows applicator attachment 200 including cap 280 (see also FIGS. 6-7). Cap 280 may be an integral part of a portion of applicator attachment 200 (e.g., such as integral with body 265 (e.g., integral plastic)) or affixed to pad 220. In the embodiment shown, cap 280 is integral with applicator attachment 200 so that a point of union of pad 220 and cap 280 constitutes interior intermediate surface 290. Cap 280 also includes interior sidewall 295 extending longitudinally from interior intermediate surface 290 to define an interior volume 298 to accept a head portion, such as head portion 120 or 140.

Sidewall 295 is shown non-continuous in that it contains spaces or gaps to allow individual portions of sidewall 295 to flex independently. It can be appreciated that sidewall 295 may be continuous by not containing spaces, and may be made of a slightly elastic material to form over a shape of head portion 120 or 140, to attach there to sufficiently for use. Suitable interior volumes (e.g., volume 298) for embodiments, include a volume having dimensions corresponding to dimensions of head portions 120 and 140 of device or tool 110, so that applicator attachment 200 can be detachably connected to device or tool 110 such as by a threaded attachment, a pressure lift attachment, a "snap-on" attachment, and a hook and loop material coupling. Moreover, also contemplated are permanent couplings of applicator attachments to devices.

Referring to FIG. 5 and sidewall 295 of cap 280, one embodiment further includes at least one protuberance 310 extending laterally from a portion of sidewall 295 into the interior volume. Thus, applicator attachment 200 may be detachably coupled to a head portion such as by snapping onto head portion 120 or 140, screwing onto head portion 120 or 140, or adhering to head portion 120 or 140 with adhesive applied to head portion 120 or 140 or to applicator attachment 200. The snapping, screwing or a force to bond the adhesive to attach applicator attachment to head portion 120 or 140 of device or tool 110 to mount it thereon may be applied by a human hand. Similarly, applicator attachment 200 may be removed from head portion 120 or 140 by unsnapping, unscrewing, or peeling of adhesives between applicator attachment 200 and head portion 120 or 140 (e.g., such as using forces applied by a human hand).

According to embodiments, the attachment between the treatment attachments and head portions may be air tight, such as by to resist leaking of a gas being pushed or pressured from holes in the surface of the head portion and into the treatment attachment. For example, the attachment between applicator attachment 200, brush attachment 300, an oxygenating treatment attachment (e.g., see oxygenating attachment 700 and porous attachment of FIGS. 8-11), a porous mass attachment, or a brush attachment having openings or pores in its base, can be attached to a head portion via threaded mating, magnetic attractive force, adhesive, heat bonding, tape, glue, or other sufficient attachment systems to allow oxygen gas to flow through the attachment to treat skin or body parts with the attachment, while resisting leaking air communicated therebetween at pressure up to 100, 200, or 300 pounds per square inch (PSI). For instance, the gas may be supplied from a source of oxygen that can be an oxygen cylinder, oxygen canister, oxygen tank including oxygen gas of up to 4,000 pounds per square inch (PSI) pressure, oxygen generator, oxygen manufacturing unit, or cartridge such as a source of oxygen external or internal and within the device or tool to which the treatment attachment is attached.

Interior intermediate surface 290 and sidewall 295 may be made of various materials and have a range of sizes. Suitable interior intermediate surface and sidewall materials include plastic, metal, composite, polyurethane, latex, rubber and resin. One suitable range for a longitudinally extending length from the interior intermediate surface a distance in the range of from 0.06 inches (1.5 mm) to 0.67 inches (17 mm). Once determinate for a length of sidewall 295 is a length sufficient to engage or be engaged by head portion 120 or 140. Likewise, suitable sizes or protuberances include protuberances extending longitudinally from a portion of the sidewall into the interior volume a distance in the range of between 0.01 inches (0.25 mm) and 0.25 inches (6.2 mm).

Cap 280 of applicator attachment 200 may also include structure within the interior volume 298 such as ridges, tapered portions, protuberances, indexing structure, posts and recesses for receiving extensions of the device, in order to more firmly attach the applicator attachment to the device. For example, as shown in FIG. 5, inner ridges 321 on interior intermediate surface 290 can be used to engage correspondingly shaped recesses in head portion 120 or 140 so that applicator attachment 200 is attached to device or tool 110 more firmly and does not rotate or slide with respect to the head portion of the device.

Figure 6:
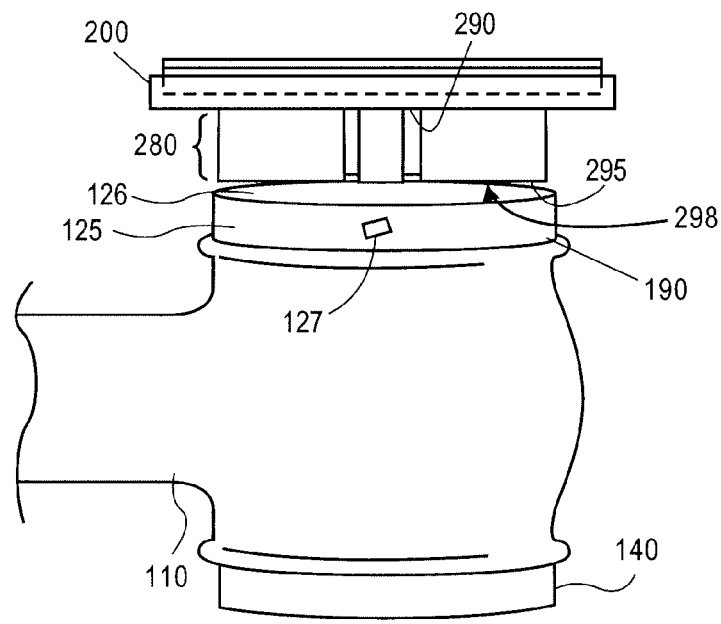
FIG. 6 is a schematic side view of the applicator attachment of FIGS. 4A and 4B prior to attachment to the head portion.

FIG. 6 is a schematic side view of the applicator attachment of FIGS. 4A and 4B prior to attachment to the head portion. FIG. 6 shows, head portion 120 is shown having an exterior shape to mate with an interior volume of a treatment attachment. For example, head portion 120 is shown having exterior sidewall 125 and exterior surface 126 to be accepted by interior volume 298 defined by interior intermediate surface 290 and interior sidewall 295 of a treatment attachment, such as applicator attachment 200, brush attachment 300, or another treatment attachment, such as those described herein.

In one embodiment, head portion 120 has a diameter on the order of about one to two inches (about 2.5 to 5 centimeters). In one embodiment, a diameter of exterior sidewall 125 is slightly larger on the order of, for example, 0.01 to 0.03 inches (one to two millimeters) than interior sidewall 295 of a treatment attachment.

It is contemplated that exterior sidewall 125 includes at least one recess to be engaged by at least one protuberance extending longitudinally from a portion of the interior sidewall into the interior volume of a treatment attachment. Specifically, exterior sidewall 125 may have recess 127 (e.g., also described above for FIGS. 1 and 2) to be engaged by protuberance 310 extending longitudinally from a portion of the interior sidewall 295 into the interior volume of a treatment attachment, such as applicator attachment 200, brush attachment 300, or another treatment attachment, as described herein.

Thus, a treatment attachment, such as applicator attachment 200 may be detachably coupled to head portion 120 such as by snapping, screwing, sliding or adhering applicator attachment 200 onto head portion 120 to engage recesses of head portion 120 (e.g., such as recess 127) with protuberances of applicator attachment 200 (e.g., such as protuberances 310) to mount it thereon, such as by a human hand. Similarly, a treatment attachment, such as applicator attachment 200 may be detached from head portion 120 such as by un-snapping, un-screwing, sliding or peeling applicator attachment 200 from head portion 120 to disengage recesses of head portion 120 (e.g., such as recess 127) with protuberances of applicator attachment 200 (e.g., such as protuberances 310) to dismount it therefrom, such as by a human hand.

Figure 7:
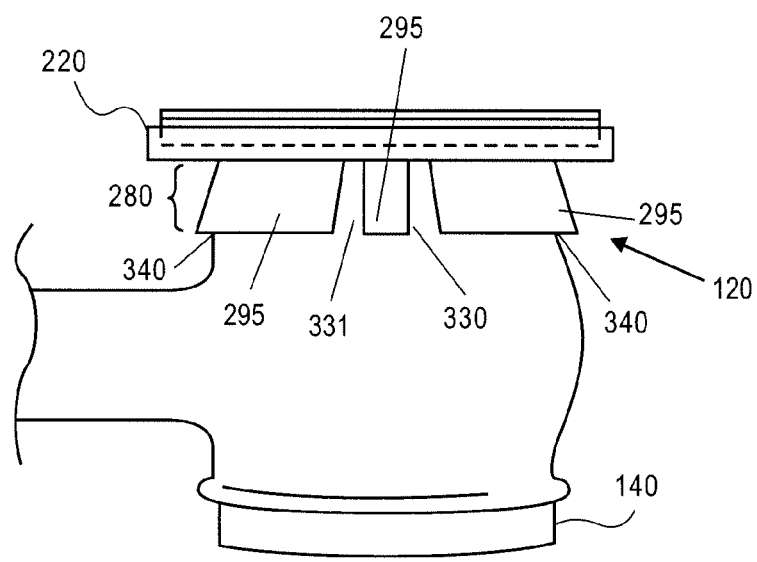
FIG. 7 is a schematic side view of the applicator attachment of FIGS. 4A and 4B after attachment to the head portion.

FIG. 7 is a schematic side view of the applicator attachment of FIGS. 4A and 4B after attachment to the head portion. Illustrated in FIG. 6 and FIG. 7 is a portion of device or tool 110 and applicator attachment 200 attached to head portion 120. FIG. 7, shows the configuration of applicator attachment 200 attached to head portion 120 of device or tool 110. In one embodiment, applicator attachment 200 is connected to head portion 110 through cap 280. As noted above, with respect to FIGS. 4-6 and the accompanying text, cap 280 includes interior intermediate surface 290 and sidewall 295 extending longitudinally from interior intermediate surface 290 and defining interior volume 298 of cap 280. As shown in FIG. 6 sidewall 295, may be a circular body having a constant diameter along the height of sidewall 295. It is also contemplated that sidewall 295, may have a shape other than circular, such as an oval, square, triangular, rectangular, polygon, curved, hexagonal, or other shape. Moreover, sidewall 295, may have a changing diameter along the height of sidewall 295, such as to form a tapered upwards or downwards surface around the height of sidewall 295.

As noted, one or more laterally extending protuberances 310 (See FIG. 5) may extend from sidewall 295 into interior volume 298 to reduce a diameter of the interior volume (when measured across one or more protuberances 310). In this manner, cap 280 does not fit easily over exterior sidewall 125 of head portion 120. In one embodiment, sidewall 295 is made of a thin plastic material that allows sidewall 295 to be deformed and depressed on (snapped) over exterior sidewall 125 onto head portion 120 of device or tool 110. In one embodiment, cap 280 is depressed on head portion 120 of device or tool 110 so that one or more protuberances 310 are positioned inferior to exterior sidewall 125. For example, exterior sidewall 125 may have recess 127 (e.g., described above for FIGS. 1, 2 and 6) may be engaged by protuberance 310 extending longitudinally into volume 298 of a treatment attachment, as described with respect to FIGS. 5-6.

FIG. 7 shows applicator attachment 200 mounted over a portion of head portion 120 through volume 298. Thus applicator attachment 200 is detachably coupled to device or tool 110 and sidewalls 295 are shown slightly flexed outward and slots 331 are wider toward device or tool 110 so that sidewalls 295 can expand to tightly fit over a portion of head portion 120 at location 340. In this embodiment, portion of sidewall 295 of applicator attachment 200 having protuberance 310 may be snapped onto head portion 120 snapping over a lip 190 to form a "snap-on" detachable coupling of applicator attachment 200 to head portion 120 of device or tool 110. Other treatment attachments described herein may be attached to head portion 120, as shown and described with respect to FIGS. 6-11, such as brush attachment 300, oxygenating attachment 700, and porous attachment 1000 (see FIGS. 8-11), and other treatment attachments described.

Furthermore, according to embodiments, a portion of sidewall 295 may be a circular body having a diameter that is slightly larger on the order of, for example, 0.01 to 0.03 inches (one to two millimeters) than the rest of sidewall 295 of head portion 120 to form a lip 190 (e.g., such as at the top of sidewall 295). In this manner, cap 280 does not fit easily over the lip of head portion 120. Thus, sidewall 295 may be made of a thin plastic material that allows sidewall 295 to be deformed and depressed on (snapped) over the lip onto head portion 120. In one embodiment, cap 280 is depressed on head portion 120 so that one or more protuberances 310 are positioned inferior to the lip (e.g., such as by being below or past the lip and closer to sidewall 295 than the extension of the outer diameter of the lip). In this embodiment, FIG. 7 may show applicator attachment 200 mounted over a portion of head portion 120 through volume 298 with a portion of sidewall 295 of applicator attachment 200 having protuberance 310 snapped onto head portion 120 by being snapped over the lip 190 to form a "snap-on" detachable coupling of applicator attachment 200 over head portion 120.

According to embodiments, treatment attachments may also attach to head portions via threaded mating, magnetic, adhesive, heat bonding, tape, glue, or other sufficient attachments. For example, head portion 120 may be threaded, have adhesive, be heat bonded, or have tape about exterior sidewall 125 and/or first end 122. In addition, head portion 120 may have a threaded opening through or a threaded mounting device on first end 122. Similarly, head portion 140 may be threaded, have adhesive, be heat bonded, or have tape about exterior sidewall 145 and/or first end 142. In addition, head portion 140 may have a threaded opening through or mounting device on first end 142.

Thus, applicator attachment 200 may attach to head portion 120 by sidewall 295 and/or another portion of applicator attachment 200 having threads to mate with those described above for head portion 120 (e.g., such as so that applicator attachment 200 screws onto head portion 120). Moreover, applicator attachment 200 may attach to head portion 120 by sidewall 295 and/or interior intermediate surface 290 to attach via adhesive, heat bonding, or tape with exterior sidewall 125 and/or first end 122. Again, it is noted that other treatment attachments may be attached to head portion 120, as shown and described above (e.g., by threads, adhesive, heat, tape, etc.), such as brush attachment 300, oxygenating attachment 700 and porous attachment 1000 (see FIGS. 8-11), and another treatment attachments described herein.

According to embodiments, various treatment attachments or types of treatment attachments may be removably attached or temporarily secured to and removed from head portion 120 of device or tool 110. For example, a treatment attachment may be replaced by switching the treatment attachment with a similar or different type of treatment attachment after none, one, or many uses. In one embodiment, applicator attachment 200 or brush attachment 300 may be removed from the device or tool 110 after use and cleaned. For example, treatment attachments may be cleaned in water, cleaning solution, cleaning powder, cleaning cloth, etc. In fact it is contemplated that tool or device 110 with treatment attachments attached, may be doused or completely immersed in water to clean the treatment attachments, and/or tool or device 110. When it is considered to be no longer useful after, for example, one or more cleanings, applicator attachment 200 or brush attachment 300 may be discarded and replaced. In addition, when treatment with a different attachment is desired, applicator attachment 200 or brush attachment 300 may be removed from the device or tool 110 and replaced with another type of treatment attachment. Device or tool 110 may then be positioned, oriented or reoriented to use the other type of attachment.

It is believed that an area of human skin or a body part may be treated with a treatment attachment attached to device or tool 110 as described above (e.g., such as to cosmetically treat, cold treat, heat treat, light treat, oxygen treat, rejuvenate, clean, polish (e.g., such as to buff), abrade, and exfoliate the skin or a body part), as a moving action of the motion generator and treatment attachment (e.g., such as of applicator attachment 200, brush attachment 300, or oxygenating attachment 700 and porous attachment 1000 of FIGS. 8-11 below) helps stimulate skin, muscle, body part, and tissue to revitalize the treated area. It is appreciated that, in use, a motion generator may or may not be used, such as in cases where the treatment attachments are moved over the skin and/or body part by the user manually moving handle 130.

It is also contemplated to abrade, exfoliate, or polish the skin or a body part with a motion generator capable of rotating or spinning the treatment attachment either in place of or in conjunction with the vibrating motion described above. For example, a motion generator having a motor with rotatable shaft connected to gears, by direct shaft, or other rotational motion transferring transmission to rotate or spin head portion 120 and/or head portion 140 may be sized to fit within interior portion 281 of device or tool 110. In an embodiment, the spinning motion generator is configured to spin the treatment attachment about a central axis of the attachment. In another embodiment, the spinning mechanism is configured to spin the treatment attachment about an off-center axis of the attachment (e.g., to produce a random orbit). A representative random or standard orbit oscillation is on the order of 6,000 or fewer revolutions per minute. One such configuration would allow an attachment such as applicator attachment 200 to be coupled to a shaft of a motor (e.g., such as motor 160 in FIG. 3).

In addition, various embodiments include a sonic wave generator disposed either within the applicator attachment, adjacent thereto, or both. In operation, sonic waves created by the sonic wave generator travel through the treatment attachment and abrade, exfoliate, cosmetically treat, rejuvenate, clean, polish, and/or massage the skin or a body part of the user. One suitable sonic wave generator is an ultrasound generator that generates sound waves from, for example, a vibrating crystal in a generator. For example, a motion generator including electronics to activate a vibrating crystal, and structure for transmitting vibration of the crystal to head portion 120 and/or head portion 140 (e.g., such as a vibration transferring material attached to the vibrating crystal and to head portion 120 and/or head portion 140) may be sized to fit within interior portion 281 of device or tool 110. The sound waves may be used to increase circulation to an area being treated.

Moreover, it is possible to light treat the skin or a body part with a laser, ultraviolet, liquid crystal display (LCD), light emitting diode (LED), or an illumination or light providing treatment attachment. For instance, treatment may be provided by a light energy providing attachment, which may or may not be in motion from a motion generator, and may or may not be used to simultaneously perform another treatment. In an embodiment, the light energy providing attachment radiates illumination onto the skin and/or body part. For instance, the light (such as laser or ultraviolet light) may be generated by a source on the light energy providing attachment or received from the head portion, or another source, and emitted or piped through the attachment. Thus the light may enter the attachment from at least one opening in the head portion and exit the attachment from at least one opening in a surface opposite the head portion. A representative illumination may be between 0.1 watt and 200 watts of light. In addition, the light energy may be provided to tool or device 110 via an external source. In some cases the light energy is provided to tool or device 110, or a tool or device having between 1 and 4 head portions, via fiber optics fibers to the attachment from a source producing between 0.1 and 10,000 Watts of light.

Specifically, a treatment attachment may be attached to head portion 120 or 140, having a light source or conduit for radiating light energy onto skin or a body part. For example, the light source or conduit may be able to illuminate skin and body parts via light, laser, ultraviolet, liquid crystal display (LCD), light emitting diode (LED), or light energy as part of a treatment. Thus, an illumination apparatus (e.g., such as laser, LED, or ultraviolet light source) and a light conduit (e.g., such as a fiber optic cable, tube, opening, and/or mirror for transferring and reflecting the laser, LED, or ultraviolet radiation to head portion 120 and/or head portion 140 and out an opening through exterior surface 126 and/or exterior surface 146) may be sized to fit within interior portion 281 of device or tool 110. Specifically, LED may exist in handle portion 130 and radiate or shoot laser light having a wavelength in the ultraviolet range towards head portion 120. A mirror proximate to head portion 120 can be used to reflect the laser light through an opening in exterior surface 126 and into an opening of an illumination or light providing treatment attachment attached to head portion 120. Such an illumination or light providing treatment attachment may include materials and surfaces described herein for other treatment attachments (e.g., such as attachments 200, 300, 700, and 1000), fiber optic cable, tubes, openings, light conduits, and/or mirrors for providing or radiating light energy or illumination (e.g., such as ultraviolet and laser light) onto the skin or a body part of a person. It is also considered that the light energy may be supplied to the skin or body part via fiber optics fibers.

Furthermore, it is possible to treat the skin or a body part with a laser, ultraviolet, liquid crystal display (LCD), light emitting diode (LED), or an illumination provided to the skin or body part from a radiating device other than a treatment attachment. For instance, treatment may be provided by a light energy providing conduit as described above, that is part of tool or device 110, a tool or device such as device 110 but having 1 head portion, 3 head portions, or 4 head portions. Specifically, a tool or device as described above may have fiber optics fibers or other light conduit exiting a handle portion or location near, above, at its top, or between one or more head portions, for providing the light energy to the skin. The source of light energy may be any source as described above.

Also, it is possible to heat treat the skin or a body part with a thermal a energy providing attachment, which may or may not be in motion from a motion generator, and may or may not be used to simultaneously perform another treatment. In an embodiment, the thermal energy providing attachment radiates heat onto the skin and/or body part. For instance the heat may be generated by a source on the thermal energy providing attachment or received from the head portion, or another source, and piped through the attachment. Thus the heat may enter the attachment from at least one opening in the head portion and exit the attachment from at least one opening in a surface opposite the head portion. A representative heating flow may be sufficient to heat a layer of skin having an area equal to that of the attachment to between 75 degrees and 500 degrees Fahrenheit.

In embodiments, a heating unit may also be disposed either within a treatment attachment, adjacent thereto, or both. In an embodiment, the heating unit is capable of heating the treatment attachment to a temperature between 75 degrees and 500 degrees Fahrenheit. The heating unit may be, for example, an infrared light, an ultraviolet light, and/or a resistive heating element connected to the power source. For example, an electrical power source, connected to insulated wires, which are in turn connected to thermally conductive coils to produce resistive heat, may be sized to fit within interior portion 281 of device or tool 110. Thus, the power source may provide sufficient current, and the thermally conductive coils may draw sufficient current, to cause the thermally conductive coils to heat up head portion 120 and/or head portion 140 and heat a treatment attachment attached thereto. The heat from the heating unit advantageously soothes the skin or a body part during treatment.

Correspondingly, it is possible to cold treat the skin or a body part with a cooling energy providing attachment, which may or may not be in motion from a motion generator, and may or may not be used to simultaneously perform another treatment. In an embodiment, the cooling energy providing attachment radiates cold onto the skin and/or body part. For instance the cold may be generated by a source on the cooling energy providing attachment or received from the head portion, or another source, and piped through the attachment. Thus the cold may enter the attachment from at least one opening in the head portion and exit the attachment from at least one opening in a surface opposite the head portion. A representative cold flow may be sufficient to cool a layer of skin having an area equal to that of the attachment to between 75 degrees and −250 degrees Fahrenheit.

In embodiments, a cooling unit may also be disposed either within a treatment attachment, adjacent thereto, or both. In an embodiment, the cooling unit is capable of cooling the treatment attachment to a temperature between 75 degrees and −250 degrees Fahrenheit. The cooling unit may be, for example, an hose supplying a cold gas or liquid, a cold substance (e.g., such as ice or dry ice) in a compartment of the attachment or head portion, a source of liquid nitrogen, etc. For example, an insulated hose to supply liquid nitrogen to cold conductive coils in the head portion to radiate cold into the treatment attachment, may be sized to fit within interior portion 281 of device or tool 110. Thus, the hose and liquid nitrogen source may provide sufficient flow, and the cold conductive coils may radiate sufficient cold, to cause the coils to cool head portion 120 and/or head portion 140 and cool a treatment attachment attached thereto. The cold from the heating unit may advantageously sooth the skin or a body part during treatment (e.g., such as by reducing swelling).

In some cases, the heat energy providing attachment and the cooling energy providing attachment may be the same attachment. For instance, a "radiator" style attachment may having tubes, conduits, vanes, coils, a core, and/or other thermally conducting structure to communicate heat or cold to skin or a body part from a liquid or gas flowing therein. The liquid or gas my be supplied from within the tool or device, or from an external supply, as described herein. Specifically, a heated or cooled liquid may be supplied to the radiator attachment and the radiator attachment may radiate the cold or heat into the skin or body part, such as during or not during other treatments as described herein. It is contemplated that the heated or cooled liquid may have a temperature sufficient to radiate heat or cold to the skin or body part between 500 degrees and −250 degrees Fahrenheit.

Next, it is possible to oxygen treat the skin or a body part with a oxygen gas provided from an oxygenating attachment, which may or may not be in motion from a motion generator, and may or may not be used to simultaneously perform another treatment. In an embodiment, the oxygenating attachment allows a gas (e.g., such as oxygen gas) to seep or be pushed through it by pressure, and chemically interact with the skin and/or body part. For instance the oxygen may enter the oxygenating attachment from openings in the head portion (e.g., such as holes through the top surface of the head portion) and exit the attachment from a surface opposite the head portion. More specifically, a source of oxygen, such as a cartridge within interior portion 281 or a tank exterior to tool or device 100 may provide oxygen to tubing, gas conduits, openings, and/or chambers within interior portion 281 to provide the oxygen to a treatment attachment attached to head portion 120 and/or head portion 140. It is contemplated that there may be a nozzle or attachment at handle 130 for transferring the oxygen to tool or device 110 and a nozzle or attachment exterior surfaces 126 and/or 146 for transferring the oxygen in tool or device 110 to a treatment attachment attached to head portion 120 and/or head portion 140. The oxygen may be supplied from a source of oxygen that can be an oxygen cylinder, oxygen canister, oxygen tank including oxygen gas of up to 4,000 pounds per square inch (PSI) pressure, oxygen generator, oxygen manufacturing unit, or cartridge such as a source of oxygen external or internal and within the device or tool to which the treatment attachment is attached.

The oxygenating attachment may be attached to a tool or device having between one and four head portions, as noted above, such as a device or tool having one, three or four head portions similar to head portions 120 and 140. Thus, in a device having three head portions, a view from above the device looking down along a longitudinal axis of the handle would show a triangular arrangement or orientation of the head portions. Similarly, in a device having four head portions, a view from above the device looking down along a longitudinal axis of the handle would show a square arrangement or orientation of the head portions.

For instance, according to embodiments, one or both head portions of device or tool 110 may include openings for venting or allowing a stream of liquid, or gas (e.g., such as oxygen or air) to exit the head portions of device or tool 110, such as to treat skin or a body part with the liquid or gas. The liquid or gas may exit device or tool 110 and enter an oxygenating attachment attached to the head portion. Thus, oxygen provided to the openings from the device or tool can enter pores of the oxygenating attachment, travel through pores of the oxygenating attachment, and exit pores on the other, far, surface of the treatment attachment, to arrive at and treat a skin surface or body part.

FIG. 8 is a schematic plan view of an embodiment of an apparatus having two head portions, where one head portion has openings there-through. FIG. 9 is a schematic side cross-sectional view of the apparatus of FIG. 8. FIGS. 8-9 show apparatus 600 having device or tool 110 that includes handle 130, head portion 140, and head portion 720. Head portion 720 includes exterior sidewall 725, exterior surface 726, and first end 722 onto which may be mounted a treatment attachment to treat an area of human skin or a body part. Exterior sidewall 725, exterior surface 726, and first end 722 may correspond to exterior sidewall 125, exterior surface 126, and first end 122 in form and function, as described above. For example, exterior sidewall 725 may include recesses, such as recesses 127 and 128.

In addition, exterior surface 726 is shown having one or more openings 710 therethrough. For example, openings 710 may be openings extending from the top of surface 726, as shown in FIG. 8, and extending therethrough to a chamber, adapter, or hose below openings 710. Thus, it is possible for a gas, such as oxygen gas or air to seep, be pressured, or be forced from below head portion 720 (e.g., such as from a chamber, adapter, or hose below head portion 720) through openings 710 and to surface 726. A representative diameter or diameter of a circle including one opening of openings 710 may be between 0.001 millimeters (mm) and 20 mm.

FIG. 8 also shows hose 732 and adapter 730 attached to tool or device 110. For example, hose 732 may be a tube for supplying a gas, such as oxygen or air, to tool or device 110, so that the gas supplied may exit openings 710. Similarly, adapter 730 may be an adapter such as for attaching to a source of gas to provide the gas to hose 732.

Adapter 730 may be attached to a source of gas, such as a source of oxygen. For example, adapter 730 may an adapter for attaching to a tank of oxygen, liquid oxygen, an oxygen generator, or an oxygen generating apparatus. In some cases, the oxygen may be supplied from a source of oxygen that can be an oxygen cylinder, oxygen canister, oxygen tank including oxygen gas of up to 4,000 pounds per square inch (PSI) pressure, oxygen generator, oxygen manufacturing unit, or cartridge such as a source of oxygen external or internal and within the device or tool to which a treatment attachment is to be attached. In addition, embodiments may include a control for controlling the volume or flow of gas, such as oxygen gas, provided to head portion 720 and/or 740. Specifically, a gas flow valve may be attached to the output of an external tank of oxygen, adapter 730, hose 732, handle portion 130, and/or hose 734 (e.g., such as to control the flow through hose 734 but having a knob or dial for controlling the flow accessible externally to handle portion 130, with or without indicia indicating various flow rates selected by manipulating or twisting the knob or handle) to control the flow of gas or oxygen flowing out of openings 710. Such a source and control of gas may supply oxygen at a pressure of between one pound per square inch (PSI) and 1000 PSI, and at a flow rate of between one and 500 milliliters per second (ml/sec).

Alternatively, according to embodiments, a source of gas, such as oxygen, may be provided within device or tool 110. For example, a cartridge or canister of gas, such as oxygen, may be disposed within handle 130 and supply the gas to hose 734. It can be appreciated that such an embodiment may include or exclude hose 732 and adapter 730. Thus, in such an embodiment, the canister or cartridge would supply gas, such as oxygen, at an appropriate pressure and flow rate as described above, such that gas would seep, be pressured, or be forced through openings 710 (e.g., with or without oxygenating attachment 700) to treat skin and body parts treated at surface 708.

According to embodiments, a treatment attachment may be attached to head portion 120, 140, or 720 having a porous material such as a cloth, sponge, a polyurethane sponge pad, a latex sponge pad, or other closed-cell sponge material having dimensions suitable for contacting an area of human skin or a body part. One suitable sponge material is commonly referred to as "make-up" sponge material, which is used representatively in the makeup arts. In one embodiment, the pore size of the sponge material ranges from 15 microns to about 410 microns. Open-cell sponge material may be used either in place of, or in conjunction with, closed-cell material. Likewise, a treatment attachment may be attached to head portion 120 or 140, having a non-porous material, such as cotton, natural or synthetic fabrics, metal, wood, cork, seaweed, synthetic rubber, paper, plastic or latex, which can be used in place of, or in conjunction with, porous material.

In one embodiment, a treatment attachment may have an applicator with a pore size that is at least as large as the average particle size of abrasive particles, as describe herein. In another embodiment, the applicator has a pore size that enables the abrasive particles to move within the applicator during manipulation of the composition over the skin or a body part. Pore sizes such as these advantageously allow the abrasive particles to recede into the applicator to prevent the skin from becoming unduly abraded or exfoliated during use. In one embodiment, the pore sizes are sufficiently small that the abrasive particles do not become so deeply-seated in the applicator that the abrasive effects of the particles is lost.

Stated differently, the pore size is established such that the level of absorption of the particles allow them to remain effective as an abrasive.

In other embodiments, the pore size may be less than the average particle size. Thus, the particles are not able to penetrate the pores and must stay on the surface or outside of the material of the treatment attachment.

Specifically, various treatment attachments may be attached to head portion 720 of FIG. 8. For example, an oxygenating attachment may be attached to head portion 720. Thus, gas, such as oxygen or air, that seeps, is pressured, or is forced through openings 710 may also seep, be pressured, or forced through an oxygenating attachment attached to head portion 720, such as to exit the side of the oxygenating attachment opposite to surface 726, in order to treat skin or a body part. A representative flow of oxygen may be between 0.1 and 20 pounds per minute.

According to embodiments, it is also possible to gas or oxygen treat the skin or a body part with a gas provided from a gas source using a head portion without a treatment attachment. The head portion may or may not be in motion from a motion generator, and may or may not be used to simultaneously perform another treatment. For instance, head portion 720 of device or tool 110 (e.g., without an oxygenating attachment or any other attachment) may allow a gas (e.g., such as oxygen gas) to seep or be pushed through it by pressure, and chemically interact with the skin and/or body part. Specifically, referring to FIG. 7, head portion 720 may be used to treat skin or a body part, such as an area or layer of human skin or a body part without a treating attachment, such as by oxygenating treatment using holes 710 without an attachment attached to head portion 720.

Alternatively, for example, FIG. 9 is a schematic side cross-sectional view of the apparatus of FIG. 8 with an oxygenating attachment mounted on head portion 720. FIG. 9 shows apparatus 600 having device or tool 110 with handle 130, head portion 140, and head portion 720. FIG. 9 also shows adapter 730 attached to hose 732 which is in turn attached to hose 734. Hose 734 is attached to chamber 736, such as a chamber disposed under openings 710 and having openings 710 extending thereto (e.g., such as where openings 710 extend from surface 726 to chamber 736). It is considered that adapter 730, hose 732, hose 734, and chamber 736 are of sufficient size and material to retain a gas, such as oxygen or air, therewithin so that the gas may be supplied to openings 710. For example, adapter 730, hoses 732 and 734, chamber 736, and openings 710 may provide a structure that when filled with a gas and pressurized is leak free of "air tight" so that the gas therewithin may be pressured or forced out of openings 710, such as into an oxygenating attachment attached to surface 726, and through the oxygenating attachment to treat skin or a body part at the surface of oxygenating attachment 700 opposite from surface 726.

Specifically, FIG. 9 shows oxygenating attachment 700 having porous material 702, center portion 706, and side portion 704. For example, center portion 706 may be an area defined within a perimeter of the center of oxygenating attachment 700, such as an area including and extending around openings 710, but not extending to the side edge of oxygenating attachment 700 (e.g., such as a side edge corresponding to exterior sidewall 125). On the other hand, side portion 704 may be defined as a portion of oxygenating attachment 700 extending around openings 710 and around the perimeter of oxygenating attachment 700 (e.g., such as extending around an area of head portion 720 corresponding to exterior sidewall 125, but not extending over openings 710). Thus, a gas, such as oxygen or air, seeping, pressured, or forced through openings 710 to surface 726 may likewise seep, be pressured, or be forced through center portion 706, but not exit side part 704 of oxygenating attachment 700. For example, such a gas may have a volume, 90% of which will exit center portion 706, while the other 10% may exit side part 704. According to embodiments, side part 704 has a porosity much less/or with much smaller pores than that of center portion 706.

In some cases oxygenating attachment 700 may not have porous material, such as when it has openings through its base surface (e.g., such as the opposite side of material attached to surface 726). For example, oxygenating attachment 700 may or may not have bristles (e.g., such as bristles 320) attached to a base surface which is attached to a head portion, and may have holes or openings through the base material at center portion 706 sufficient to communicate or let pass a gas, such as oxygen or air, seeping, pressured, or forced through openings 710 to surface 726 and through the opening in the base material of the oxygenating attachment. Suitable base materials may be layers of metal, plastic, adhesive material, and other materials described above for forming applicator attachment 200.

FIG. 9 also shows oxygenating attachment 700 having surface 708, such as a surface of oxygenating attachment 700 opposite that of pad 220 of head portion 720 when oxygenating attachment 700 is attached to head portion 720. Thus, such gas may be used to treat skin or a body part, such as skin or a body part being treated by surface 708 of oxygenating attachment 700.

Oxygenating attachment 700 includes porous material 702, such as including abrasive, non-abrasive, sponge, porous, or other material having one or more natural and/or synthetic material, such as a plastic, a nylon, a polyurethane, a latex, a polymer, a composite, a rubber, a cloth, a polyurethane sponge pad, a latex sponge pad, or other closed-cell sponge material having dimensions suitable for contacting an area of human skin or a body part. In embodiments, porous material 702 may be a material having openings or conduits extending from surface 726 to surface 708, such as openings or conduits sufficient to allow a gas, such as oxygen, steam, water, or fluid, to be received by porous material 702 from surface 726 and be expelled from surface 708. Also, porous material 702 can have abrasive particles in, on, as part of, and/or at the tip of the bristles suitable to treat skin and body parts.

It is contemplated that surface 708 may be an abrasive surface such as described above with respect to surface 126. Moreover, porous material 702 may include abrasive particles, such as described above with respect to pad 220. Moreover, according to embodiments, oxygenating attachment 700 may be used to apply a solution, compound, abrasive particles, cream, or other treatment substance, cold, heat, light, or other treatment substance, or treatment, as described herein.

Oxygenating attachment 700 may be attached to head portion 720, such as by adhesive, tape, or "snap-on", or screwed on, or attached otherwise as described above with respect to attaching applicator attachment 200 to head portion 120. For example, oxygenating attachment 700 may include a structure similar to cap 280 in order to be snapped on to head portion 720.

According to embodiments, a sponge, porous, or oxygenating attachment, as described above may be used to treat skin, human hair, scalp, cuticles, and other body parts. For example, an oxygenating attachment can be used to treat skin and other body parts by manipulating device or tool 110 (e.g., with or without moving with a motion generator a head portion on which the oxygenating attachment is attached), while a supply of gas, such as oxygen, is provided to the skin and/or body part from surface 708 via head portion 720.

Treatment attachments, such as a brush attachment 300, oxygenating attachment 700, a heating unit attachment, a cooling unit attachment; a light source attachment, a porous mass attachment, and a sponge pad attachment, as described above, may be made of plastic, metal, electronic circuitry, printed circuit board, polyurethane, sponge pad, latex, and/or nylon, polymer. Also, such a treatment attachment may attach to a head portion as described above for applicator attachment 200 (e.g., such as by being attachable to a head portion by adhesive, screw on, or "snap-on" as described above with respect to FIGS. 6-7).

Embodiments include a method of manipulating treatment attachments over an area of human skin or a body part with device or tool 110 having a handle portion coupled to moving head portions and suitable for gripping by a human hand to treat skin or a body part as described above. Movement of the head portions can include vibrating, spinning and propagating sonic waves therethrough, as described above.

Hence, according to embodiments, a tool or device having a treatment attachment as described herein may apply or be used to treat skin and body parts by applying pressure and moving the treatment attachment across the skin and/or body part with upward circular, back and forth, random, or other movement. Also, a device or tool for use in treating skin and body parts may include a handle for grasping by a human hand, a power source to drive or activate a motion generator to move two head portions on which to attach two treatment attachments used to treat skin and/or body parts. It is likewise considered that a device or tool for treating skin and body parts may include a handle for grasping by a human hand, but not have a power source or motion generator, such that one or more treatment attachments attached to two head portions may be used to treat skin and body parts by manipulating the handle to move the treatment attachment(s) over the skin and/or body part. Such treatment attachments may include an abrasive applicator attachment; a porous attachment; an oxygenating attachment; a porous applicator attachment; an applicator attachment for applying a paste, a bar, a cream, a liquid, and/or an abrasive particles; a sponge applicator attachment; a porous mass attachment; a brush attachment having abrasive bristles; a brush attachment having soft without abrasive bristles; a soft pad buffer attachment; and other treatment attachments appropriate for treating areas of skin, hair, scalp, cuticles, face, limbs, torso, hands and feet of a person.

According to embodiments, skin or a body part can be treated by an oxygenating treatment device that does not include device or tool 110. Such an oxygenating treatment device may correspond to the description above of an oxygenating treatment attachment. Specifically, such a oxygenating treatment device may be oxygenating treatment attachment 700, an oxygenating brush attachment to supply oxygen to skin or a body part, an oxygenating treatment attachment having bristles, oxygenating treatment attachment not having bristles, a porous attachment, or a porous mass attachment as described herein, attached to a source of gas, such as oxygen as described herein, where the oxygenating treatment device can be sufficiently manipulated by a human hand without device or tool 110 to treat skin or a body part (e.g., such as hair).

Figure 10:
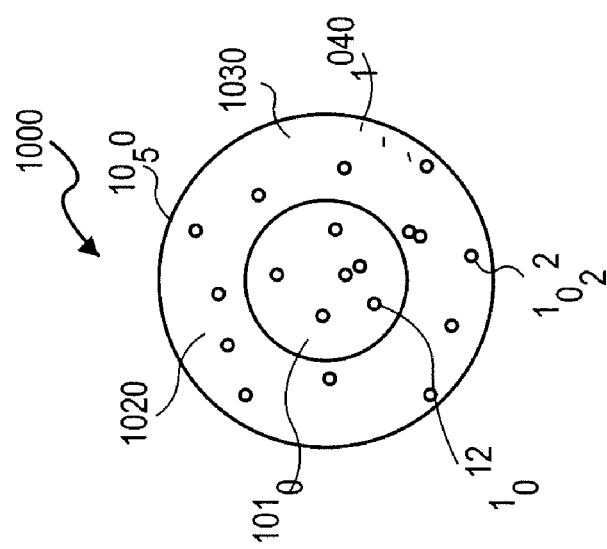
FIG. 10 shows a porous attachment for treating an area of skin or body part with a gas, such as oxygen.

Thus, such an oxygenating treatment device can gas or oxygen treat the skin or a body part with a gas provided from a gas source using to the device via a tube, hose, chamber, or adapter below the surface of the oxygenating treatment device. The gas source may be a tank, tube, cartridge, cannister, or other source as described above for supplying gas or oxygen to device or tool 110 or to oxygenating treatment attachment 700. The supplied gas may then exit openings in the surface of the oxygenating treatment device to treat the skin or body part. Specifically, the oxygenating treatment device allows a gas (e.g., such as oxygen gas) to seep or be pushed through it by pressure, and chemically interact with the skin and/or body part. According to embodiments, the attachment may be moved over the skin or body part only by manipulating the oxygenating treatment device sides, back, or a handle of the oxygenating treatment device. The oxygenating treatment device may or may not be used to simultaneously perform another treatment. In an embodiment, the oxygenating treatment device FIG. 10 shows a porous attachment for treating an area of skin or body part with a gas, such as oxygen. FIG. 10 shows porous attachment 1000 having center portion 1010 and donut-shaped outer portion 1020. Porous attachment 1000 includes side portions 1050 surrounding outer portion 1020. Porous attachment 1000 also has a surface for attaching to a tool or device to be held by a human hand, surface 1030. Opposite to surface 1030 is a surface to provide a gas to treat an area of skin or body part, surface 1040.

Outer portion 1020 and/or center portion 1010 may have outer perimeters defining various shapes, including a circular shape, an oval shape, a teardrop shape, or a polygon shape. In addition, outer portion 1020 and/or side portion 1050 may define, have or encircle a diameter of between 0.5 and 8 inches, such as a diameter of 0.5 inch, 1 inch, 1.25 inch, 1.5 inch, 1.75 inch, 2 inches, 2.5 inches, 2.75 inches, 3 inches, 3.25 inches, 3.5 inches, 4 inches, 5 inches, 6 inches, or 7 inches. Outer portion 1020 and/or center portion 1010 may define or have a thickness of between 0.2 inches and 8 inches, such as by having a thickness of 5 millimeters, 10 millimeters, 15 millimeters, 18 millimeters, 19 millimeters, 20 millimeters, 21 millimeters, 22 millimeters, 25 millimeters, 35 millimeters, 50 millimeters, 75 millimeters, 80 millimeters, or 100 millimeters.

Center portion 1010 includes a porous material, such as a material through which gas, such as oxygen, may seep or be pressured. Similarly, outer portion 1020 may include a porous material as described above with respect to center portion 1010. Specifically, outer portion 1020 and/or center portion 1010 may include a porous material as described above for oxygenating attachment 700, a sponge attachment, or a porous attachment. Side portions 1050 may include or may not include porous material, such as porous material described with respect to center portion 1010.

It is considered that the arrangement of pores, lack of pores, and/or direction of pores in outer portion 1020 and/or sidewalls 1050 may prohibit gas supplied to center portion 110 from escaping or seeping out of outer portion 1020 or sidewalls 1050. For instance, FIG. 10 shows center portion 1010 having pores such as pore 1012 extending from surface 1030 to surface 1040, and outer portion 1020 having pores such as pore 1022 extending from surface 1030 to surface 1040. Thus, a gas introduced to pores in center portion 1010 at surface 1030 may seep out or be pressured out of pores in outer portion 1020 and/or center portion 110 at surface 1040 to treat skin or a body part disposed adjacent to or in contact with surface 1040. It is considered that outer portion 1020 of porous attachment 1000 may be attached to a tool or device for manipulation by a human hand, such that a gas may be supplied to center portion 1010 at surface 1030 and flow through, seep through or be pressured through pores in center portion 1010 and to outer portion 1020 and/or center portion 110 at surface 1040.

According to embodiments, at surface 1030, outer portion 1020 may have a base, and/or an adhesive to attach porous attachment surface 1030 to a head portion of a tool or device, or to a device having a surface for grasping and manipulation by a human hand. It is considered that at surface 1030, outer portion 1020 may have a non-porous base material, such as cotton, natural or synthetic fabrics, metal, wood, cork, seaweed, synthetic rubber, paper, plastic or latex. Surface 1030 of the base material may have an adhesive thereon, such as a "tape" with a covering that can be removed prior to attaching surface 1030 to a device for manipulation by a human hand.

For instance, porous attachment 1000 may be attached to a tool or device having between one and four head portions, as noted above, such as a device or tool having one, three or four head portions similar to head portions 120 and 140. Thus, porous attachment 1000 may be attached to a tool or device for manipulation by a human hand, similar to tool or device 110 but having only one head portion, such as having only head 120, but not having head 140. It is also contemplated that porous attachment 1000 may be attached to a tool or device having a motion generator or not having a motion generator as described herein.

Figure 11:
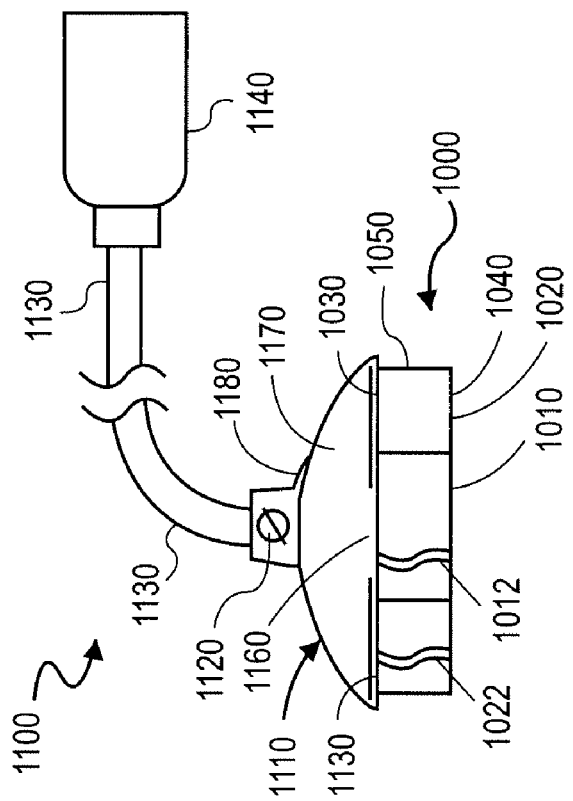
FIG. 11 shows the porous attachment of FIG. 10 attached to a tool or device for manipulation by a human hand.

According to embodiments, porous attachment 1000 may be a porous attachment, sponge attachment, or oxygenating attachment 700, as described above. In addition, embodiments include porous attachment 1000 for attaching to a device having a physical dimension for grasping and manipulating by a human hand, but not having handle 130 or a motorized motion generator therein. For example, FIG. 11 shows the porous attachment of FIG. 10 attached to a tool or device for manipulation by a human hand. FIG. 11 shows system 1100 including porous attachment 1000 attached to surface 1130 of oxygen diffuser 1110, about opening 1160. System 1100 also includes valve 1120 for adjusting a flow of oxygen received by diffuser 1110 from hose 1130. Hose 1130 is attached to valve 1120 and oxygen source 1140. Oxygen source 1140 may be a source of oxygen similar to those described above with respect to oxygenating attachment 700. Diffuser 1110 has chamber 1170 coupled to hose 1130 via valve 1120.

Opening 1160, may be an opening having a sufficient size or diameter to allow a gas supplied to chamber 1170 to seep or be pressured from chamber 1170 into center portion 1010, such as to be pressured or to seep through pores, such as pore 1012, and to exit surface 1040 to treat an area of skin or a body part therebelow or in contact with surface 1040. Specifically, opening 1060 may be an opening having or defining a diameter between 1 millimeter and 3 centimeters, such as by having a diameter of 2 millimeters, 3 millimeters, 4 millimeters, 5 millimeters, 7 millimeters, 9 millimeters, 10 millimeters, or 12 millimeters.

Gas supplied to valve 1120 may flow into chamber 1170 and out of opening 1160. From opening 1160 gas may seep or be pressured into center portion 1010 of porous attachment 1000. Hence, valve 1120 may have a knob or dial for controlling the flow of gas or oxygen received from hose 1130 to diffuser 1110 to flow out of pores in center portion 1010 at surface 1040 to a pressure of between one pound per square inch (PSI) and 1000 PSI, a flow rate of between one and 500 milliliters per second (ml/sec).

FIG. 11 also shows system porous attachment 1000 having surface 1180 having a physical dimension for grasping and manipulating by a human hand. For example, surface 1180 may be grasped and manipulated similarly to the descriptions above for handle portion 130. In some cases, surface 1180 may be grasped and manipulated by fingers and thumbs of a person to maneuver surface 1040 over and/or on skin or body parts of a person to treat the skin and/or body parts with a gas, such as oxygen, during or not during other treatments as described herein.

Therefore, porous attachment 1000 and system 1100 can be used to treat an area of skin or body part, such as by holding surface 1080 with hand while oxygen is being supplied via surface 1040 to the skin or body part. Moreover, attachment 1000 may be attached to a tool or device to treat an area of skin with a cream, a cleaning solution, a buffing solution, an abrasive substance, or other treatment lotion, cream, or substance as described herein. Specifically, porous attachment 1000 and/or system 1100 may be used to treat an area of skin or body part by supplying a gas, such as oxygen, to the skin or body part, where such gas or oxygen pushes, forces, or presses a cream, solution, or substance into the skin or body part during treatment. For example, the cream, solution, or substance may be applied to surface 1040 of porous attachment 1000, or may be applied to the skin or body part, prior to applying surface 1040 of porous attachment 1000 to the skin or body part for treatment.

Figure 12:
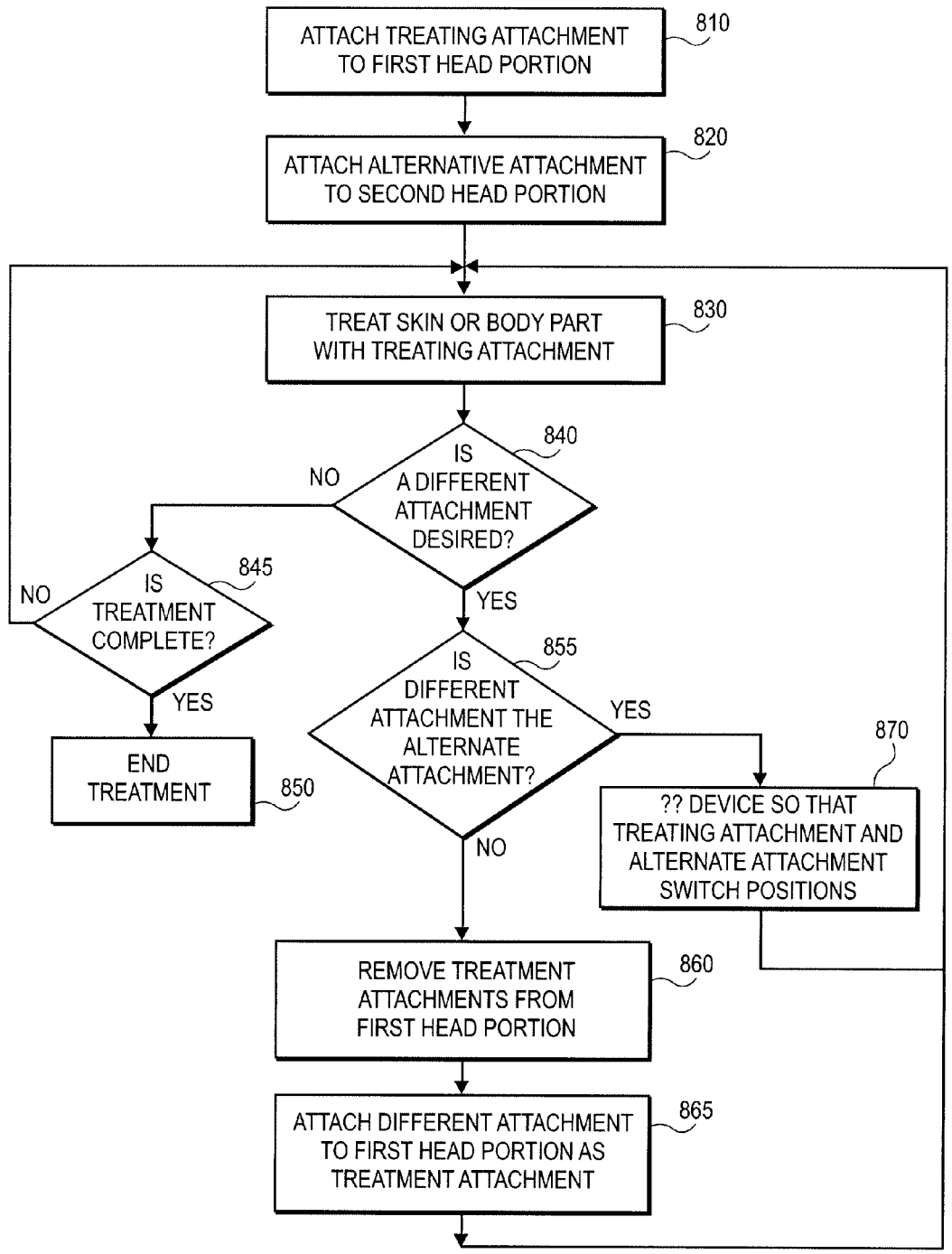
FIG. 12 is a flow chart describing one embodiment of an operation to treat skin.

FIG. 12 is a flow chart describing one embodiment of an operation to treat skin or a body part. The flow chart of FIG. 12 may illustrate a method utilizing device or tool 110 and treatment attachments described with respect to FIGS. 1-11 (e.g, such as applicator attachment 200, brush attachment 300, oxygenating attachment 700, a heating unit attachment, a cooling unit attachment; a light source attachment, a porous mass attachment, and a sponge pad attachment).

At block 810, a treating attachment is attached to the first head portion of a treatment device. For example, block 810 may correspond to a human user attaching applicator attachment 200 to head portion 120 of treatment device or tool 110. At block 820, an alternate attachment is attached to a second head portion. Block 820 may correspond to a human user attaching brush attachment 300 to head portion 140 of treatment device or tool 110.

At block 830, skin or a body part, such as an area or layer of human skin or a body part, is treated with the treating attachment. For example, block 830 may correspond to a human user using device or tool 110 to treating an area of skin or a body part with applicator attachment 200, with or without a treatment composition.

In some embodiments, block 830 may correspond to treating skin or a body part, such as an area or layer of human skin or a body part, is treated with device or tool 110 without a treating attachment (e.g., such as oxygenating treatment using holes 710 without an attachment thereto).

At block 840, it is determined whether a different attachment is desired as the treating attachment to treat the skin or a body part. For example, block 840 may correspond to a human user deciding whether a current period for treating an area or layer of skin or a body part with the treatment attachment is complete. If at block 840 it is determined that a different attachment is not desired, then the process continues to block 845.

At decision block 845, it is determined whether the treatment of the skin or a body part is complete. For example block 845 may correspond to a human user deciding if treatment of an area or layer of skin or a body part using all available or desired treatment attachments is complete. In one instance, treatment may be complete if the area or layer of skin or a body part has been exfoliated with applicator attachment 200, cleaned and/or polished with brush attachment 300, to a human user's satisfaction. If at block 845 it is determined that treatment is not complete, the process returns to block 830. Alternatively, if at block 845 it is determined that treatment is complete, the process continues to block 850 where treatment ends.

If at block 840 it is determined that a different attachment is desired as the treating attachment, then the process continues to block 855. At decision block 855, it is determined whether the different attachment is the alternate attachment. Block 845 may correspond to a human user deciding whether the different attachment desired is brush attachment 300. If at block 855 it is determined that the different attachment desired is the alternate attachment, the process continues to block 870.

At block 870, the device is reoriented so that the treating attachment and the alternate attachment switch positions. For example, block 870 may correspond to a human user rotating treatment device or tool 110 about its axis so that the alternate attachment is oriented, reoriented, or positioned to treat an area or layer of skin or a body part desired to be treated (e.g., so that the alternate attachment is in the position that the treating attachment previously was in so that the alternate attachment is now the treating attachment). For example, block 870 may correspond to rotating device or tool 110 about its longitudinal axis so that the position of head portion 140 and head portion 120 are switched (e.g., thus, brush attachment 300 will be switched into the position that applicator attachment 200 was in, causing brush attachment 300 to now be the treating attachment). After block 870, the process returns to block 830. 1301 If at block 855 it is determined that the different attachment is not the alternate attachment, the process continues to block 860. For example, block 855 may correspond to a human user deciding that brush attachment 300 is not the different attachment desired to be used to treat the skin and/or body part.

At block 860, the treatment attachment is removed from the first head portion. For example, block 860 may correspond to a human user removing applicator attachment 200 from head portion 120. After block 860, the process continues to block 865.

At block 865, the different attachment desired is attached to the first head position and becomes the treatment attachment. Block 865 may correspond to a human user attaching a treatment attachment other than applicator attachment 200 or brush attachment 300 to head portion 120. Specifically, a sponge applicator attachment, a porous mass attachment, soft pad buffer attachment, or other treatment attachment appropriate for treating areas of human skin or a body part may be applied in place of applicator attachment 200 on head portion 120. Thus, the different attachment now becomes the treatment attachment to treat the skin or a body part. After block 865, the process returns to block 830.

According to embodiments, treating an area or layer of skin or a body part at block 830 may or may not include applying and/or using heat, cold, light, composition or solution as described above. For example, a composition or solution used may include moisturizer, abrasive particles, cleaning solution, and/or polishing solution disposed on the applicator or bush attachment. This can be accomplished either by dipping the applicator or brush attachment into a container with the composition or solution disposed inside or by disposing the composition or solution directly onto the applicator or brush attachment (e.g., with a dispenser, a squirt bottle tube, spatula or other suitable means). It is also considered that a composition or solution may be applied to a surface of a treatment attachment (e.g., such as onto bristles, abrasive surface, or porous surface of an attachment), skin, or body part by hand (e.g., such as by applying composition or solution onto a treatment attachment, face, neck, hands, feet, skin or a body part the user of the device). The treatment attachment may then be used to perform treatment, with the composition or solution.

The user may then apply the composition or solution disposed on the applicator or brush attachment to the area of skin or a body part to be treated. One example is applying approximately one-quarter inch of the composition or solution across the entire surface of a porous applicator, or abrasive or soft bristle brush attachment. Another example is applying approximately one-quarter inch of the composition or solution across the entire surface of surface 726 of head portion 720. The user then dots the area to be treated at locations on the order of, for example, one to three inches apart.

Subsequently, the user may manipulate the heat, cold, light, composition or solution over the area of skin or a body part to be treated by manipulating the handle of tool or device or tool 110 while the treatment attachment is moved by the user and/or motion generator (e.g., such as by being vibrated). In an embodiment, manipulation of the heat, cold, light, composition or solution is characterized by moving the handle so that the applicator or brush attachment travels over an area of skin or a body part using upward circular or randomly directed strokes. In one example, the manipulation of the heat, cold, light, composition or solution is continued for one to ten minutes or until the composition or solution has been worked into, cleaned, and/or polished the skin or a body part and the skin or a body part appears soft and smooth.

In an embodiment, a user manipulates the handle to treat acne, large pores, sluggish skin, and/or acne scars by moving the applicator or brush attachment while the attachment is also moved by the motion generator, as described above, on the area of skin having the acne or acne scars to abrade, exfoliate, clean, and/or polish the skin (e.g., such as to minimize any rough skin areas including acne scars). This may include applying a pressure to the skin or a body part with a treatment attachment and moving the treatment attachment across the face and neck using slight upward circular or randomly directed motions.

In another example, a user manipulates the treatment attachment on the skin while the attachment is also moved by the motion generator to softening calluses by manipulating the attachment, as described above, on damp or dry skin to minimize any rough skin areas (including extremely rough and thick calluses) such as heals, feet or cuticles. More particularly, a composition or solution, such as an embodiment described above, can be applied to clean dry skin and body parts using the applicator or brush attachment. With respect to rejuvenating, cleansing, and/or polishing hands and/or feet, such uses may include applying a pressure to the skin with the attachment and moving the attachment across the hands and feet using slight upward circular or randomly directed motions. It is contemplated that in the examples herein, a user may manipulate the treatment attachment on the skin and/or body part while the attachment is not moved by a motion generator It should also be noted that in applying a composition or solution to the skin, the user may dab the composition or solution on certain areas of the skin and/or body parts before manipulating the composition or over the skin and/or body parts with a treatment attachment. Alternatively, the user may simultaneously apply the composition or solution to the skin and/or body part and manipulate the composition over the area of skin and/or body part to be treated. Moreover, the user may shake abrasive particles, composition or solution onto the skin and/or body parts, such as from a "shaker" like a salt shaker, before or during manipulating the treatment attachment over the skin and/or body part. Also, the user may simultaneously apply the composition or solution to the treatment attachment, dot the area to be treated and manipulate in rotary strokes. Using the treatment attachment, the user may manipulate the attachment with the motion generator in the on (generating motion) position, or in the off position for a lighter treatment (e.g., such as a treatment where the user is manually treating the area by moving the treatment attachment over the area by manipulation of the handle of device or tool 110). Finally, if a composition or solution is used, the user may wipes off any unabsorbed portion of the composition or solution and may optionally rinse the area (e.g., such as with water).

It is to be understood that even though numerous characteristics and advantages of various embodiments have been set forth in the foregoing description, together with details of structure, function, and formulations of the various embodiments, this disclosure is illustrative only. Changes may be made in detail, especially matters of structure, management of parts, and compositional or solution formulation, without departing from the scope of the various embodiments as expressed by the broad general meaning of the terms of the appended claims.

What is claimed:

1. An apparatus comprising:
   a first head portion;
   a second head portion;
   a handle portion coupled to the first head portion and to the second head portion, the handle portion and suitable for gripping by a human hand;
   wherein the handle portion comprises a motion generator to move one of the first head portion and the second head portion, the first head portion includes a first end to removably attach to a first attachment to treat epidermal skin, and the second head portion includes a second end to removably attach to a second attachment to treat epidermal skin,
   wherein the first head portion includes a first end to removably attach to an oxygenating attachment to apply a treatment gas to a localized area of human skin, a plurality of openings extending through the first end to allow the treatment gas to travel from the first head portion to the oxygenating attachment.

2. The apparatus of claim 1, further comprising a switch to cause the motion generator to move either the first head portion or the second head portion sufficiently to abrade the skin using one of an abrasive surface, abrasive bristles, or an abrasive composition.

3. The apparatus of claim 1, wherein the motion generator comprises a motor coupled to an eccentric mass to move at least one of the first head portion and the second head portion.

4. The apparatus of claim 1, wherein the motion generator comprises:
   a motor and a plurality of gears to at least one of spin and vibrate the first head portion or the second head portion.

5. The apparatus of claim 1, wherein the motion generator comprises:
   a sonic wave generator to propagate one of sonic and ultrasonic waves through at least one of the first head portion and the second head portion.

6. The apparatus of claim 1, wherein the second attachment comprises a brush attachment to brush a localized area of human skin or a body part.

7. The apparatus of claim 6, wherein the first head portion comprises an exterior shape to mate with an interior volume of the oxygenating attachment.

8. The apparatus of claim 6, wherein first head portion comprises an exterior sidewall and an exterior surface to be accepted by an interior volume defined by an interior intermediate surface and an interior sidewall of the oxygenating attachment.

9. The apparatus of claim 8, wherein the exterior sidewall has at least one recess to be engaged by at least one protuberance extending longitudinally from a portion of the interior sidewall into the interior volume.

10. The apparatus of claim 6, wherein the second head portion comprises an exterior shape to mate with an interior volume of the brush attachment.

11. The apparatus of claim 6, wherein second head portion comprises an exterior sidewall and an exterior surface to be accepted by an interior volume defined by an interior intermediate surface and an interior sidewall of the brush attachment.

12. The apparatus of claim 11, wherein exterior sidewall has at least one recess to be engaged by at least one protuberance extending longitudinally from a portion of the interior sidewall into the interior volume.

13. The apparatus of claim 6, wherein the brush attachment comprises:
   a first end having dimension suitable for mating with the second head portion, and a second end comprising a plurality of bristles having dimensions suitable for contacting localized areas of human hair or skin.

14. The apparatus of claim 13, wherein the plurality of bristles define a generally polygon shape.

15. The apparatus of claim 13, wherein the plurality of bristles comprise one of a plurality of one of abrasive bristles for abrading or exfoliating areas of human skin, and a plurality soft bristles for polishing or cleansing areas of human hair or skin.

16. The apparatus of claim 1, wherein the oxygenating attachment comprises:
   a first end having dimension suitable for attaching to the first head portion with one of an adhesive and a double sided tape, and a second end comprising a surface having dimensions suitable for contacting localized areas of human hair or skin.

17. The apparatus of claim 16, wherein the oxygenating attachment comprises:
   a porous material having a generally discus shape with a sidewall and a center portion defined within the sidewall;
   wherein the center portion has a porosity that is greater than a porosity of the sidewall.

18. The apparatus of claim 1, wherein the motion generator is to move both the first and the second head portions.

19. The apparatus of claim 1, wherein the motion generator is a physical attachment between the handle portion and the head portion such that movement of the motion generator causes movement of the head portion over a skin surface or a body part of a person.

20. The apparatus of claim 1, wherein the first end and the second end are on opposing outer surfaces of a head.

21. An apparatus comprising:
   a head attached to a handle;
   a first head portion of the head;

an oxygenating attachment configured to treat human epidermus, the oxygenating attachment removably attached to the first head portion, wherein the first head portion includes a first end to removably attach to the oxygenating attachment to apply a treatment gas to a localized area of human skin, a plurality of openings extending through the first end to allow the treatment gas to travel from the first head portion to the oxygenating attachment;

a motion generator to move the first head portion to treat a localized area of human epidermus using the attachment; and a second head portion of the head, the second head portion opposing the first head portion and configured to be removably attached to an attachment configured to treat human epidermis.

22. A method comprising:

moving at least one of a first head portion coupled to a handle of an apparatus and a second head portion coupled to the handle with a motion generator of the apparatus;

manipulating a handle portion of the apparatus to treat an area of epidermal human skin with one of a first treatment attachment removably coupled to the first head portion and a second treatment attachment removably coupled to the second head portion, wherein the first head portion includes a first end to removably attach to an oxygenating attachment to apply a treatment gas to a localized area of human skin, a plurality of openings extending through the first end to allow the treatment gas to travel from the first head portion to the oxygenating attachment.

23. The method of claim 22, wherein moving the first head portion and moving the second head portion includes moving either the first head portion or the second head portion at the same time.

24. The method of claim 22, further comprising:

orienting the handle portion to treat an area of human skin with a second treatment attachment coupled to the second head portion.

25. The method of claim 24, wherein orienting comprises:

applying a plurality of bristles of a brush attachment to a layer of human hair or skin;

manipulating the brush attachment to brush the layer of human hair or skin with the plurality of bristles to one of clean particles off of the layer of human skin, and polish the layer of human skin.

26. The method of claim 24 further comprising one of removably attaching the first treatment attachment to the first head portion and removably attaching the second treatment attachment to the second head portion.

27. The method of claim 22, wherein the second head portion opposes the first head portion.

\* \* \* \* \*